(12) United States Patent
Ginsberg et al.

(10) Patent No.: US 8,530,621 B2
(45) Date of Patent: Sep. 10, 2013

(54) COMBINED PREPARATION OF A THIAZIDE DIURETIC AND A LOOP DIURETIC

(75) Inventors: Mark Ginsberg, San Diego, CA (US); Anthony William Partridge, Montreal (CA); Iain Campbell, Oxford (GB); Kate Louise Wegener, Adelaide (AU)

(73) Assignee: The Regents of the University of California, Oakland, CA (US)

( * ) Notice: Subject to any disclaimer, the term of this patent is extended or adjusted under 35 U.S.C. 154(b) by 438 days.

(21) Appl. No.: 12/523,037

(22) PCT Filed: Jan. 14, 2008

(86) PCT No.: PCT/US2008/051016
§ 371 (c)(1),
(2), (4) Date: Apr. 26, 2010

(87) PCT Pub. No.: WO2008/089152
PCT Pub. Date: Jul. 24, 2008

(65) Prior Publication Data
US 2010/0210525 A1 Aug. 19, 2010

Related U.S. Application Data

(60) Provisional application No. 60/884,693, filed on Jan. 12, 2007.

(51) Int. Cl.
*A61K 38/04* (2006.01)
(52) U.S. Cl.
USPC ........................................................ 530/324
(58) Field of Classification Search
None
See application file for complete search history.

(56) References Cited

U.S. PATENT DOCUMENTS

2003/0224993 A1  12/2003  Land et al.
2008/0085271 A1*  4/2008  Anderson et al. ............ 424/94.5

OTHER PUBLICATIONS

Wegener, KL Crystallography and Bioinformatics Department of Biochemistry University of Cambridge, 2H7E, pp. 1-3, Jun. 2, 2006.*
Shuker et al. Discovering High-Affinity Ligands for Proteins: SAR by NMR. Science New Series, 274(5292):1531-1534, 1996.*
Kong et al. Structural basis for the phosphorylation-regulated focal adhesion targeting of type Igamma phosphatidylinositol phosphate kinase (PIPKIgamma) by talin. J Mol Biol. May 26, 2006;359(1):47-54.*
Ling et al. Tyrosine phosphorylation of type Igamma phosphatidylinositol phosphate kinase by Src regulates an integrin-talin switch. (J. Cell. Biol. 163, 1339-1349, 2003.*
Wegner et al. Structural Basis of Integrin Activation by Talin. Cell. 129:171-182, Jan. 12, 2007.*
Wegener, K.L., et al., "Structural Basis of Integrin Activation by Talin," Cell vol. 128(1): 171-182 (2007).

Ratnikov B.I "Integrin Activation by Talin," J. Thrombosis Haemostasis, 3: 1783-1790 (2005).
Garcia-Alvarez, B et al., "Structural Determinants of Integrin Recognition by Talin," Molecular Cell, 11: 49-58 (2003).
Tadokoro, S., et al., "Talin Binding to Integrin Beta Tails: A Final Common Step in Integrin Activation," Science, 302: 103-106 (2003).
Patil, S., et al., "Identification of a Talin-binding Site in the Integrin Beta 3 Subunit Distinct from the NPLY Regulatory Motif of Post-ligand Binding Functions," J. Biol. Chem., 274(40): 28575-28583 (1999).
Abrams, C., et al., "Determinants of specificity of a baculovirus-expressed antibody Fab fragment that binds selectively to the activated form of integrin alpha IIb beta 3," J Biol Chem 269, 18781-18788 (1994).
Ayed, A., et al., "Latent and active p53 are identical in conformation," Nat Struct Biol 8, 756-760 (2001).
Baker, E. K., et al., "A genetic analysis of integrin function: Glanzmann thrombasthenia in vitro," Proc Natl Acad Sci U S A 94, 1973-1978 (1997).
Bennett, J. S., "Structure and function of the platelet integrin alpha II beta3," J Clin Invest 115, 3363-3369 (2005).
Bersch, B., et al., "Optimized set of two-dimensional experiments for fast sequential assignment, secondary structure determination, and backbone fold validation of 13C/15N-labelled proteins," J Biomol NMR 27, 57-67 (2003).
Brunger, A. T., et al., "Crystallography & NMR system: A new software suite for macromolecular structure determination." Acta Crystallogr D Biol Crystallogr 54, 905-921 (1998).
Calderwood, D. A., et al., "Integrin beta cytoplasmic domain interactions with phosphotyrosine-binding domains: a structural prototype for diversity in integrin signaling," Proc Natl Acad Sci U S A 100, 2272-2277 (2003).
Calderwood, D. A., et al., "The phosphotyrosine binding-like domain of talin activates integrins," J Biol Chem 277, 21749-21758 (2002).
Campbell, I. D. and Ginsberg, M.H "The talin-tail interaction places integrin activation on FERM ground," Trends Biochem Sci 29, 429-435 (2004).
Chishti, A. H., et al.,"The FERM domain: a unique module involved in the linkage of cytoplasmic proteins to the membrane," Trends Biochem Sci 23, 281-282 (1998).
Cornilescu, G., et al., "Protein backbone angle restraints from searching a database for chemical shift and sequence homology," J Biomol NMR 13, 289-302 (1999).

(Continued)

*Primary Examiner* — Maher Haddad
(74) *Attorney, Agent, or Firm* — Sutherland Asbill & Brennan LLP

(57) ABSTRACT

The specific molecular basis of the interaction between talin and integrin $\beta_3$ has been defined. This specific interaction provides a new therapeutic target; agents that can disrupt this specific interaction should be useful therapeutic agents for a number of significant diseases and conditions including inflammation, heart disease, including myocardial infarction, and tumor metastasis. The present invention includes a chimeric peptide that has high affinity for talin, muteins of talin and integrin $\beta_3$ as well as screening methods for agents that can disrupt the interaction between talin and integrin $\beta_3$.

6 Claims, 13 Drawing Sheets

(56) References Cited

OTHER PUBLICATIONS

Critchley, D. R. "Genetic, biochemical and structural approaches to talin function," Biochem Soc Trans 33, 1308-1312 (2005).

De Pereda, J. M., et al., "Structural basis for phosphatidylinositol phosphate kinase type Igamma binding to talin at focal adhesions," J Biol Chem 280, 8381-8386 (2005).

Delaglio, F., et al., "NMRPipe: a multidimensional spectral processing system based on UNIX pipes," J Biomol NMR 6, 277-293 (1995).

Edwards, S. D., and Keep, N. H., "The 2.7 A crystal structure of the activated FERM domain of moesin: an analysis of structural changes on activation," Biochemistry 40, 7061-7068 (2001).

Farrow, N. A.,et al., "Backbone dynamics of a free and phosphopeptide-complexed Src homology 2 domain studied by 15N NMR relaxation," Biochemistry 33, 5984-6003 (1994).

Ginsberg, M. H., et al., "Integrin regulation," Curr Opin Cell Biol 17, 509-516 (2005).

Gottschalk, K. E., "A coiled-coil structure of the alphaIIbbeta3 integrin transmembrane and cytoplasmic domains in its resting state," Structure 13, 703-712 (2005).

Hamada, K., et al.. "Structural basis of the membrane-targeting and unmasking mechanisms of the radixin FERM domain," Embo J 19, 4449-4462 (2000).

Han, B. G., et al.,"Protein 4.1R core domain structure and insights into regulation of cytoskeletal organization," Nat Struct Biol 7, 871-875 (2000).

Horwitz, A., et al., "Interaction of plasma membrane fibronectin receptor with talin—a transmembrane linkage," Nature 320, 531-533 (1986).

Huang, C. L., et al., "Disabled-2 is a negative regulator of integrin alpha(IIb)beta(3)-mediated fibrinogen adhesion and cell signaling," J Biol Chem 279, 42279-42289 (2004).

Hughes, P. E., et al., "Breaking the integrin hinge. A defined structural constraint regulates integrin signaling," J Biol Chem 271, 6571-6574 (1996).

Hughes, P. E., et al., "The conserved membrane-proximal region of an integrin cytoplasmic domain specifies ligand binding affinity," J Biol Chem 270, 12411-12417 (1995).

Hynes, R. O., "Integrins: bidirectional, allosteric signaling machines," Cell 110, 673-687 (2002).

Koradi, R., et al.. "MOLMOL: a program for display and analysis of macromolecular structures," J Mol Graph 14, 51-55, 29-32 (1996).

Laskowski, R. A., et al., "AQUA and PROCHECK-NMR: programs for checking the quality of protein structures solved by NMR," J Biomol NMR 8, 477-486(1996).

Li, W., et al., "A push-pull mechanism for regulating integrin function," Proc Natl Acad Sci U S A 102, 1424-1429 (2005).

Luo, B. H., et al., "Disrupting integrin transmembrane domain heterodimerization increases ligand binding affinity, not valency or clustering," Proc Natl Acad Sci U S A 102, 3679-368 (2005).

Papagrigoriou, E., et al., "Activation of a vinculin-binding site in the talin rod involves rearrangement of a five-helix bundle," Embo J 23, 2942-2951 (2004).

Pardi, A., et al., "Calibration of the angular dependence of the amide proton-C alpha proton coupling constants, 3JHN alpha, in a globular protein. Use of 3JHN alpha for identification of helical secondary structure," J Mol Biol 180, 741-751 (1984).

Partridge, A. W., et al., "Transmembrane domain helix packing stabilizes integrin alphaIIbbeta3 in the low affinity state," J Biol Chem 280, 7294-7300 (2005).

Pickford, A. R., et al., "The hairpin structure of the (6)F1(1)F2(2)F2 fragment from human fibronectin enhances gelatin binding," Embo J 20, 1519-1529 (2001).

Redfield, C., et al., "Secondary structure and topology of human interleukin 4 in solution," Biochemistry 30, 11029-11035 (1991).

Rees, D. J., et al, "Sequence and domain structure of talin," Nature 347, 685-689 (1990).

Shattil, S. J., et al., "Changes in the platelet membrane glycoprotein IIb.IIIa complex during platelet activation," J Biol Chem 260, 11107-11114 (1985).

Smith, W. J., et al., "Structure of the active N-terminal domain of Ezrin. Conformational and mobility changes identify keystone interactions," J Biol Chem 278, 4949-4956 (2003).

Stefansson, A., et al., "Determination of N- and C-terminal borders of the transmembrane domain of integrin subunits," J Biol Chem 279, 21200-21205 (2004).

Tanentzapf, G., et al., "An interaction between integrin and the talin FERM domain mediates integrin activation but not linkage to the cytoskeleton," Nat Cell Biol 8: 601-606 (2006).

Uhlik, M. T., et al., "Structural and evolutionary division of phosphotyrosine binding (PTB) domains," J Mol Biol 345, 1-20 (2005).

Ulmer, T. S., et al., "Domain-specific interactions of talin with the membrane-proximal region of the integrin beta3 subunit," Biochemistry 42, 8307-8312 (2003).

Vinogradova, O., et al., "Membrane-mediated structural transitions at the cytoplasmic face during integrin activation," Proc Natl Acad Sci U S A 101, 4094-4099 (2004).

Vinogradova, O., et al., "A structural mechanism of integrin alpha(IIb)beta(3) "inside-out" activation as regulated by its cytoplasmic face," Cell 110, 587-597 (2002).

Weljie, A. M., et al.,"Solution structures of the cytoplasmic tail complex from platelet integrin alpha IIb- and beta 3-subunits," Proc Natl Acad Sci U S A 99, 5878-5883 (2002).

\* cited by examiner

A.

B.

US 8,530,621 B2

SEQUENCE LISTING

```
<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Asp Thr Ala Asn Asn Pro Leu Tyr Asp Glu Ala
1               5                   10

<210> SEQ ID NO 2
<211> LENGTH: 35
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Phospho-Tyr

<400> SEQUENCE: 2

Lys Lys Leu Leu Ile Thr Ile His Asp Arg Lys Glu Phe Ala Lys Phe
1               5                   10                  15

Glu Glu Glu Arg Ala Arg Ala Lys Trp Val Tyr Ser Pro Leu His Tyr
            20                  25                  30

Ser Ala Arg
        35

<210> SEQ ID NO 3
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Leu Leu Ile Thr Ile His Asp Arg Lys Glu Phe Ala Lys Phe Glu
1               5                   10                  15

Glu Glu Arg Ala Arg Ala Lys Trp Asp Thr Ala Asn Asn Pro Leu Tyr
            20                  25                  30

Lys Glu Ala Thr Ser Thr Phe Thr Asn Ile Thr Tyr Arg Gly Thr
        35                  40                  45

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Trp Asp Thr Ala Asn Asn Pro Leu Tyr Lys Glu
1               5                   10

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Leu Ile Thr Ile His Asp Arg Lys Glu Phe Ala Lys Phe Glu
1               5                   10                  15

Glu Glu Arg Ala Arg Ala Lys Trp Asp
            20                  25

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Lys Leu Leu Ile Thr Ile His Asp Arg Lys Glu Phe Ala Lys Phe Glu
1               5                   10                  15

Glu Glu Arg Ala Arg Ala Lys Trp
            20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Leu Leu Ile Thr Ile His Asp Arg Lys Glu Phe Ala Lys Phe Glu
1               5                   10                  15

Glu Glu Arg Ala Arg Ala Lys
            20

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phospho-Tyr

<400> SEQUENCE: 8

Val Tyr Ser Pro Leu His Tyr Ser Ala Arg
1               5                   10

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Phospho-Tyr

<400> SEQUENCE: 9

Lys Leu Leu Ile Thr Ile His Asp Arg Lys Glu Phe Ala Lys Phe Glu
1               5                   10                  15

Glu Glu Arg Ala Arg Ala Lys Trp Val Tyr Ser Pro Leu His Tyr Ser
            20                  25                  30

Ala Arg
```

COMBINED PREPARATION OF A THIAZIDE DIURETIC AND A LOOP DIURETIC

PRIORITY APPLICATIONS

This application claims the benefit of priority under 35 USC §119(e) from U.S. Provisional Application Ser. No. 60/884,693, filed Jan. 12, 2007, the disclosure of which is incorporated by reference herein in its entirety.

GOVERNMENT SUPPORT

This invention was made with government support under GM064346 and HL078784 awarded by National Institutes of Health. The government has certain rights in this invention.

SEQUENCE LISTING

The instant application contains a Sequence Listing which has been submitted in ASCII format via EFS-Web and is hereby incorporated by reference in its entirety. Said ASCII copy, created on Jan. 9, 2013, is named 24978185.txt and is 3,844 bytes in size.

BACKGROUND OF THE INVENTION

This invention is directed to the interaction between integrin $\beta_3$ and talin, including a chimeric peptide that has high affinity for talin, muteins of integrin $\beta_3$ and talin, and screening methods for identifying agents that can disrupt the interaction, which provides a new therapeutic target.

Regulation of integrin affinity (activation) is essential for metazoan development and for many pathological processes. Integrins are found throughout the animal kingdom where they play important roles in cell adhesion, migration, proliferation, and survival. They are membrane-spanning heterodimers of $\alpha$ and $\beta$ subunits, both of which typically comprise a short cytoplasmic tail (~20 to 50 residues), a single transmembrane helix, and a large extracellular domain (~700 to 1000 residues). In mammals, there are eighteen identified $\alpha$ subunits and eight $\beta$ subunits that combine to form 24 distinct heterodimers. In humans, integrins play critical roles in development and participate in the pathogenesis of heart disease, chronic inflammation, and cancer.

Many integrins are expressed with their extracellular domains in a default low-affinity ligand binding state (the "off state"); however, cells can change the conformation and affinity of these receptors in response to cellular stimulation, a process often termed "integrin activation." This conformation change results in increased adhesion and subsequent signaling, mediating events such as cell migration, platelet aggregation, leukocyte exit from the vasculature, and assembly of the extracellular matrix. The binding of a cytoskeletal protein, called talin, to the $\beta$ subunit cytoplasmic tail is a common final step in the activation process.

Because integrin activation is involved in pathophysiological processes leading to such conditions as cancer, heart disease including myocardial infarction, and rheumatoid arthritis, there have been a number of pharmacological efforts to control such activation. One route that has been tried is integrin antagonists such as ReoPro (abciximab), Integrilin (eptifibatide), Aggrestat (tirofiban), Raptiva, or Tysabri (natalizumab). These bind to and block all integrin function. The blockage of all integrin function can lead to substantial side effects. For example, the administration of Tysabri (natalizumab) for treatment of multiple sclerosis was shown in rare cases to lead to the development of progressive multifocal leukoencephalopathy, causing suspension of approval of Tysabri. Another route that has been tried is the use of anti-thrombotics that block integrin activation indirectly. Although some of these drugs, such as Plavix (clopidogrel), naproxen, or acetylsalicylic acid (aspirin), are useful, they also have very wide ranging effects and have significant side effects that limit their use in many patients.

Therefore, there is a need to develop targets of pharmacological action that are specific to the integrin and have specific mechanism-based effects. This will result in fewer side effects and enable their use in a wider variety of patients.

SUMMARY OF THE INVENTION

One aspect of the present invention is an isolated complex comprising a structural interface between talin and integrin $\beta_3$ such that the complex is between talin and membrane-proximal amino acid residues of the integrin $\beta_3$ tail.

Another aspect of the present invention is a chimeric peptide comprising:
(1) a tryptophan residue that binds to a pocket on the surface of a talin molecule;
(2) a sufficient number of $\beta_3$ integrin tail residues on the amino-terminal side of the tryptophan residue of (1); and
(3) a sufficient number of PIPKIγ residues on the carboxyl-terminal side of the tryptophan residue to (1) to form a binding site in conjunction with (1) and (2);
wherein the chimeric peptide is soluble and has higher affinity for talin than $\beta_3$ integrin tail.

Another aspect of the present invention is a derivative of the chimeric peptide described above wherein the derivative has an affinity for talin at least as great as the chimeric peptide from which the derivative is formed.

Another aspect of the present invention is a method for blocking integrin $\beta_3$ activation comprising the step of administering the chimeric peptide of claim 2 to a organism in a quantity sufficient to disrupt the specific binding interaction between integrin $\beta_3$ and talin and thereby to block integrin $\beta_3$ activation.

Another aspect of the present invention is an isolated integrin $\beta_3$ mutein that is selected from the group consisting of the mutein F727A and the mutein F730A. Similarly, another aspect of the present invention is an isolated domain of an isolated integrin $\beta_3$ mutein that is selected from the group consisting of the mutein F727A and the mutein F730A that competes with naturally-occurring integrin $\beta_3$ for binding to talin at least about 80% as effectively as the complete integrin $\beta_3$ mutein on a molar basis.

Another aspect of the present invention is an isolated talin mutein that has at least one mutation selected from the group consisting of L325R, S365D, S379R, and Q381V with the proviso that the mutein is folded in substantially the same way as wild-type talin as determined by their dispersed NMR spectra. Similarly, another aspect of the present invention is an isolated domain of a talin mutein that has at least one mutation selected from the group consisting of L325R, S365D, S379R, and Q381V with the proviso that the mutein is folded in substantially the same way as wild-type talin as determined by their dispersed NMR spectra that competes with naturally occurring talin at least about 80% as effectively as the complete talin mutein on a molar basis for binding with integrin $\beta_3$.

Additional aspects of the present invention include nucleic acid molecules encoding proteins or peptides according to the present invention, vectors, including expression vectors, and host cells transformed or transfected with the nucleic acid molecules or vectors.

Yet another aspect of the present invention is a screening method to detect an agent that blocks integrin $\beta_3$ activation comprising the steps of:

(1) determining the extent of interaction between the chimeric peptide of the present invention as described above and talin in the presence of an agent to be screened by NMR spectroscopy;

(2) determining the extent of interaction between the chimeric peptide and talin in the absence of the agent to be screened by NMR spectroscopy; and (3) comparing the extent of interaction between the chimeric peptide and talin in the presence of the agent and in the absence of the agent to determine whether the agent blocks integrin $\beta_3$ activation.

Still another aspect of the present invention is a method for screening for alteration in talin function comprising the steps of:

(a) determining the extent of interaction between talin from a subject suspected of having an alteration in talin function and the chimeric peptide of the present invention as described above by NMR spectroscopy; and (b) comparing the extent of interaction found in (a) with the extent of interaction between normal talin and the chimeric peptide as determined by NMR spectroscopy in order to detect or determine the existence of an alteration in talin function.

BRIEF DESCRIPTION OF THE DRAWINGS

The following invention will become better understood with reference to the specification, appended claims, and accompanying drawings, where:

FIG. 8 shows weighted shift maps (see Experimental Procedures) obtained by observing $^1$H-$^{15}$N HSQC spectra on addition of different peptides to talin F3. Because of the unfavorable exchange rates, the data for the full-length β3 peptide was obtained from intensity measurements (see text) and in this case, negative values are indicated in yellow.

FIG. 9 shows intramolecular NOEs that define the interface between talin and the membrane proximal (MP) region of the β3 integrin tail. A. Two segments of the two-dimensional NOESY spectrum recorded on a sample of the β3/PIPKIγ chimera peptide and the talin F3 sub-domain (1:1) ratio in D$_2$0 (full sample details are given in the Experimental Procedures). B. Structure of the interface between the MP region of the integrin tail and the talin F3 sub-domain, showing the intermolecular NOEs as dashed blue lines. For clarity, side-chains of residues not involved in the interface are not shown. In addition, the only protons shown are those involved in the intermolecular NOEs. Talin side-chains are indicated in yellow and the talin backbone in pale yellow. Integrin side-chains are shown in red and the integrin backbone in orange. The location of this interface in the context of the whole complex is indicated to the left.

FIG. 10 shows heteronuclear $^{15}$N-$^1$H NOEs for the talin F3 domain alone (red) and in complex with the /PIPKIγ peptide (green) or the β3/PIPKIγ chimeric peptide (blue), showing that the loop between strands S1 and S2 is rigidified by the β3/PIPKIγ peptide but not by the PIPKIγ peptide. Thus, this effect is due to the membrane proximal (MP) region of the β3 integrin tail. Elements of secondary structure are indicated.

FIG. 11 shows representative raw flow cytometry data for A5 cells transfected with WT, Q381V and L325R talin. F23 indicate talin mutations of membrane-proximal-contacting residues prevent activation of WT integrin and inhibit the activity of a high-affinity chimeric integrin. CHO cells stably expressing WT human αIIbβ3 (A5 cells) were transiently co-infected with vectors for WT or mutant AH-tagged talin F23 and eGFP protein as a transfection marker. Activation level of the integrin in harvested cells was measured by flow cytometry using the PAC-1 antibody. Specific PAC-1 binding was measured by PAC1 staining in the present or absence of Ro43-5054 (see Experimental Procedures). WT talin F23 activated the integrin whereas empty vector and L325R talin did not. Q381V talin F23 had greatly diminished levels of activation. Quantitative bar graphs of these results are shown in FIG. 3 as well.

FIG. 12 shows representative isothermal calorimetry data for WT talin F3 binding to WT chimeric peptide. Peptide concentrations were typically at 150 to 300 μM while protein concentrations ranged from 25 to 50 μM. For the W359A mutant, the protein concentration was 50 μM and the peptide concentration was 1 mM. Prior to ITC titrations, the peptides and proteins were in buffer consisting of 200 mM Tris, 300 mM NaCl, pH 7.5. All experiments were conducted at 23 degrees Celsius. The top panel shows the real-time data trace, with each spike corresponding to a single injection of peptide into the protein-containing cell. The bottom panel is the binding curve, calculated using the software program Origin.

DETAILED DESCRIPTION OF THE INVENTION

Figure 1:
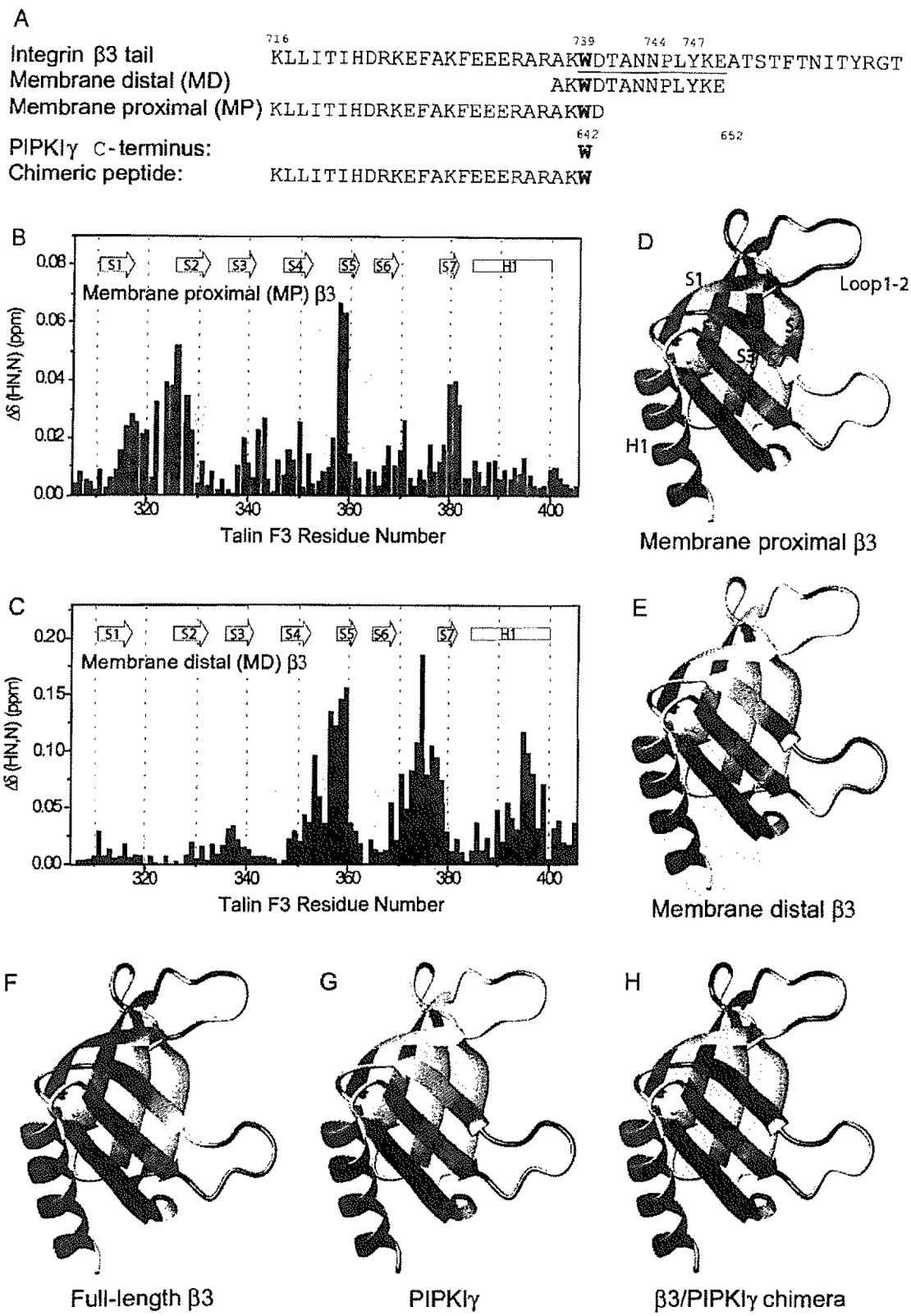
FIG. 1 shows NMR titration studies of integrin and PIPKIγ peptides. A. Design of peptides (SEQ ID NOS: 3-6, respectively, in order of appearance). B-C. Weighted shift maps (see Experimental Procedures) of induced chemical shifts seen in $^1$H-$^{15}$N HSQC spectra when the MP peptide (SEQ ID NO: 5) (B.) and MD peptides (SEQ ID NO: 4) (C.) are added to the talin F3 sub-domain. D-H. Weighted shift data for each peptide titration are mapped onto the structure of the F3 subdomain, with largest shifts shown in blue. D. MP peptide (SEQ ID NO: 5). E. MD peptide (SEQ ID NO: 4). F. Full-length β3 integrin tail (SEQ ID NO: 3). Because of the unfavorable exchange rates, the data for the full-length β3 peptide were obtained from intensity measurements. G. PIPKIγ peptide. H. β3/PIPKIγ chimeric peptide (SEQ ID NO: 6).

In accordance with the present invention and as used herein, the following terms and abbreviations are defined with the following meanings, unless explicitly stated otherwise. These explanations are intended to be exemplary only. They are not intended to limit the terms as they are described or referred to throughout the specification. Rather, these explanations are meant to include any additional aspects and/or examples of the team as described and claimed herein.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically thereto. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156).

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA). As used herein, the terms "encoding" or "encoded" when referring to a protein or polypeptide of defined sequence include all nucleic acid sequences that encode the protein or polypeptide of defined sequence, including nucleic acid sequences that differ from the naturally-occurring sequence by the degeneracy of the genetic code, unless such sequences are excluded. It is well known in the art that many amino acids are encoded by multiple codons, and that many nucleic acid sequences can therefore encode the same protein or polypeptide sequence.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manlier as naturally occurring amino acids. In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4$^{th}$ Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or Ile; Phe/Met or Leu or Tyr; Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or Ile), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

Polypeptides of the invention can be produced either from a nucleic acid disclosed herein by expression of the nucleic acid in a system that is capable of such expression, or by the use of standard techniques of molecular biology and chemistry. For example, a truncated protein of the invention can be produced by expression of a recombinant nucleic acid of the invention in an appropriate host cell, or alternatively by a combination of ex vivo procedures, such as protease digestion and purification.

As used herein to refer to a protein or nucleic acid molecule, the terms "isolated" and/or "purified" are used interchangeably to refer to a state in which the protein or nucleic acid molecule of interest is typically found in nature, and in which the protein or nucleic acid molecule of interest is substantially free of other molecules that would interfere with the activity of the protein or nucleic acid molecule that is being assayed or employed.

For example, the term "purified" can refer to a preparation in which the protein or nucleic acid molecule of interest is 50%, 60%, 70%, 75%, 80%, 85%, 90%, 95%, 97.5%, 99%, 99.9%, or 99.99% pure, or one of still greater purity. Methods for the isolation of protein and nucleic acid molecules are well known in the art.

As used herein, the term "comprising" means including, but not limited to, whatever follows the word "comprising". Thus, use of the term "comprising" indicates that the listed elements are required or mandatory, but that other elements are optional and may or may not be present.

As used herein, the term "consisting of" means including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The present invention demonstrates the molecular basis of the interaction between the talin and the membrane-proximal integrin $\beta_3$ domain and provides a new target for therapeutic intervention to treat diseases and conditions such as inflammation, autoimmune diseases, heart disease including myocardial infarction, and cancer. This target can be specifically used to modulate the talin-integrin $\beta_3$ interaction without the side effects that occur with presently available therapeutic agents and methods.

In particular, the interaction between talin and integrin $\beta_3$ occurs in the F3 sub-domain of the FERM domain of talin (see Example). This interaction is the proposed site of therapeutic intervention. The F3 sub-domain has a phosphotyrosine (PTB) binding domain fold. Disruption of the newly identified interactions blocks integrin activation in cells while retaining binding to the membrane-distal (MD) region of $\beta 3$. These results define the talin/integrin interactions that lead to integrin activation and explain why talin is unique among PTB-containing proteins in its activating ability. They also identify an interaction that is a target for the rational design of therapeutics that block integrin activation; the new understanding also allows the engineering of cells or animals with selective defects in integrin activation.

Accordingly, one aspect of the present invention is an isolated complex comprising a structural interface between talin and integrin $\beta_3$. The isolated complex comprises a complex between talin and membrane-proximal amino acid residues of the integrin $\beta_3$ tail. This structural interface is the actual site of the talin/integrin $\beta_3$ interaction.

Another aspect of the present invention is a chimeric peptide comprising: (1) a tryptophan residue that binds to a pocket on the surface of a talin molecule; (2) a sufficient number of $\beta_3$ integrin tail residues on the amino-terminal side of the tryptophan residue of (1); and (3) a sufficient number of PIPKI$\gamma$ residues on the carboxyl-terminal side of the tryptophan residue to (1) to form a binding site in conjunction with (1) and (2); wherein the chimeric peptide is soluble and has higher affinity for talin than $\beta_3$ integrin tail.

Still another aspect of the present invention is a derivative of the chimeric peptide described above retaining substantial binding affinity for talin. The derivative has an affinity for talin at least 80% as great as the chimeric peptide described above. Typically, the derivative of the chimeric peptide has no more than two conservative amino acid substitutions, as defined below. Preferably, the derivative of the chimeric peptide has no more than one conservative substitution.

Still another aspect of the present invention is a method for blocking integrin $\beta_3$ activation comprising the step of administering the chimeric peptide as described above or a derivative thereof as described above to a organism in a quantity sufficient to disrupt the specific binding interaction between integrin $\beta_3$ and talin and thereby to block integrin $\beta_3$ activation. This method can be used to treat conditions or diseases characterized by integrin $P_3$ activation, such as myocardial infarction, tumor metastasis, or rheumatoid arthritis.

Yet another aspect of the present invention is an isolated integrin $\beta_3$ mutein that is selected from the group consisting of the mutein F727A and the mutein F730A. These muteins have utility for blocking integrin $\beta_3$ activation; they act as competitive inhibitors with naturally occurring integrin $\beta_3$. Therefore, they act to inhibit the specific interaction between integrin $\beta_3$ and talin. In another alternative, the isolated integrin $\beta 3$ mutein can be incorporated in a fusion protein including at least one additional protein domain. The at least one additional protein domain can have therapeutic activity or can have another desirable property such as increased stability or solubility. In still another alternative, the isolated integrin $\beta_3$ mutein can be conjugated to a therapeutic moiety for the treatment of a condition such as myocardial infarction, cancer, or rheumatoid arthritis.

Yet another aspect of the present invention is an isolated domain of an integrin $\beta_3$ mutein as described above that competes with naturally-occurring integrin $\beta_3$ for binding to talin at least about 80% as effectively as the complete integrin $\beta_3$ mutein on a molar basis. Preferably, the isolated domain is at least 30 amino acids in length and includes residues that are both membrane-distal and membrane-proximal to the tryptophan residue that occur at position 739 of the wild-type integrin $\beta_3$ molecule. More preferably, the isolated domain is at least 50 amino acids in length; still more preferably, it is at least 100 amino acids in length.

Yet another aspect of the present invention is an isolated talin mutein that has at least one mutation in the F3 region of talin; the mutation can be L325R, S365D, S379R, or Q381V, or a combination of more than one of these mutations, with the proviso that the mutein is folded in substantially the same way as wild-type talin as determined by their dispersed NMR spectra. These isolated talin muteins can be used as competitive inhibitors of the talin-integrin $\beta_3$ interaction in the same way as the integrin $\beta_3$ muteins described above. The talin muteins can also be incorporated into fusion proteins or conjugated to a therapeutic moiety as described above.

Yet another aspect of the present invention is an isolated domain of a talin mutein as described above that competes with naturally occurring talin at least about 80% as effectively as the complete talin mutein on a molar basis for binding with integrin $\beta_3$. Preferably, the isolated domain includes the F3 subdomain of the FERM domain of talin and includes a phosphotyrosine binding domain fold therein; more preferably, the isolated domain includes the F2 and F3 subdomains of the FERM domain of talin.

Still another aspect of the present invention is an isolated and purified nucleic acid molecule encoding one of: (1) the chimeric peptide described above; (2) a derivative of the chimeric peptide as described above; (3) the isolated integrin $\beta_3$ mutein as described above; (4) an isolated domain of the integrin $\beta_3$ mutein as described above; (5) the isolated talin mutein as described above; or (6) an isolated domain of the talin mutein as described above. The nucleic acid can be DNA or RNA, but is typically DNA.

Yet another aspect of the present invention is a vector including therein the isolated and purified nucleic acid molecule described above. The vector can be an expression vector.

Still another aspect of the present invention is a host cell transformed or transfected with a nucleic acid molecule according to the present invention or a vector according to the present invention. The host cell can be prokaryotic or eukaryotic, as described below.

With respect to nucleotide sequences that are within the scope of the invention, all nucleotide sequences encoding the polypeptides that are embodiments of the invention as described are included in nucleotide sequences that are within the scope of the invention. This further includes all nucleotide sequences that encode polypeptides according to the invention that incorporate conservative amino acid substitutions as defined above.

Nucleic acid sequences of the present invention further include nucleic acid sequences that are at least 95% identical to the sequences above, with the proviso that the nucleic acid sequences retain the activity of the sequences before substitutions of bases are made, including any activity of proteins that are encoded by the nucleotide sequences and any activity of the nucleotide sequences that is expressed at the nucleic acid level. Preferably, the nucleic acid sequences are at least 97.5% identical. More preferably, they are at least 99% identical. For these purposes, "identity" is defined according to the Needleman-Wunsch algorithm (S. B. Needleman & C. D. Wunsch, "A General Method Applicable to the Search for Similarities in the Amino Acid Sequence of Two Proteins," *J. Mol. Biol.* 48: 443-453 (1970)).

Nucleotide sequences encompassed by the present invention can also be incorporated into a vector, including, but not limited to, an expression vector, and used to transfect or transform suitable host cells, as is well known in the art. The vectors incorporating the nucleotide sequences that are encompassed by the present invention are also within the scope of the invention. Host cells that are transformed or transfected with the vector or with polynucleotides or nucleotide sequences of the present invention are also within the scope of the invention. The host cells can be prokaryotic or eukaryotic; if eukaryotic, the host cells can be mammalian cells, insect cells, or yeast cells. If prokaryotic, the host cells are typically bacterial cells.

Transformation of a host cell with recombinant DNA may be carried out by conventional techniques as are well known to those skilled in the art. Where the host is prokaryotic, such as *Escherichia coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used.

A variety of host-expression vector systems may be utilized to express the protein or peptide coding sequence. These include but are not limited to microorganisms such as bacteria transformed with recombinant bacteriophage DNA, plasmid DNA or cosmid DNA expression vectors containing a protein or peptide coding sequence; yeast transformed with recombinant yeast expression vectors containing the protein or peptide coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a protein or peptide coding sequence; insect cell systems infected with recombinant virus expression vectors (e.g., baculovirus) containing a protein or peptide coding sequence; or animal cell systems infected with recombinant virus expression vectors (e.g., retroviruses, adenovirus, vaccinia virus) containing a protein or peptide coding sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., Methods in Enzymology, 153:516-544, 1987). For example, when cloning in bacterial systems, inducible promoters such as pL of bacteriophage λ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted zinc finger-nucleotide binding polypeptide coding sequence.

In bacterial systems a number of expression vectors may be advantageously selected depending upon the use intended for the protein or polypeptide expressed. For example, when large quantities are to be produced, vectors which direct the expression of high levels of fusion protein products that are readily purified may be desirable. Those which are engineered to contain a cleavage site to aid in recovering the protein are preferred. Such vectors include but are not limited to the *Escherichia coli* expression vector pUR278 (Ruther, et al., EMBO J., 2:1791, 1983), in which the protein or peptide coding sequence may be ligated into the vector in frame with the lac Z coding region so that a hybrid lac Z protein is produced; pIN vectors (Inouye & Inouye, Nucleic Acids Res. 13:3101-3109, 1985; Van Heeke & Schuster, J. Biol. Chem. 264:5503-5509, 1989); and the like.

In yeast, a number of vectors containing constitutive or inducible promoters may be used. For a review, see Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, 1986, IRL Press, Wash., D.C.). Alternatively, vectors may be used which promote integration of foreign DNA sequences into the yeast chromosome.

In cases where plant expression vectors are used, the expression of a protein or peptide coding sequence may be driven by any of a number of promoters. For example, viral promoters such as the 35S RNA and 19S RNA promoters of CaMV (Brisson, et al., Nature, 310:511-514, 1984), or the coat protein promoter to TMV (Takamatsu, et al., EMBO J., 6:307-311, 1987) may be used; alternatively, plant promoters such as the small subunit of RUBISCO (Coruzzi, et al., EMBO J. 3:1671-1680, 1984; Broglie, et al., Science 224: 838-843, 1984); or heat shock promoters, e.g., soybean hsp17.5-E or hsp17.3-B (Gurley, et al., Mol. Cell. Biol., 6:559-565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421-463, 1988; and Grierson & Corey, Plant Molecular Biology, 2d Ed., Blackie, London, Ch. 7-9, 1988.

An alternative expression system that can be used to express a protein or peptide of the invention is an insect system. In one such system, *Autographa californica* nuclear polyhedrosis virus (AcNPV) is used as a vector to express foreign genes. The virus grows in *Spodoptera frugiperda* cells. The protein or peptide coding sequence may be cloned into non-essential regions (in *Spodoptera frugiperda*, for example, the polyhedrin gene) of the virus and placed under control of an AcNPV promoter (for example the polyhedrin promoter). Successful insertion of the protein or peptide coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. (E.g., see Smith, et al., J. Biol. 46:584, 1983; Smith, U.S. Pat. No. 4,215,051).

Eukaryotic systems, and preferably mammalian expression systems, allow for proper post-translational modifications of expressed mammalian proteins to occur. Therefore, eukaryotic cells, such as mammalian cells that possess the cellular machinery for proper processing of the primary transcript, glycosylation, phosphorylation, and, advantageously secretion of the gene product, are the preferred host cells for the expression of a protein or peptide according to the present invention. Such host cell lines may include but are not limited to CHO, VERO, BHK, HeLa, COS, MDCK, 293, and WI38.

Mammalian cell systems that utilize recombinant viruses or viral elements to direct expression may be engineered. For example, when using adenovirus expression vectors, the coding sequence of a protein or peptide according to the present invention may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the protein or peptide according to the present invention in infected hosts (e.g., see Logan & Shenk, Proc. Natl. Acad. Sci. USA 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA, 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the desired gene in host cells (Cone & Mulligan, Proc. Natl. Acad. Sci. USA 81:6349-6353, 1984). High level expression may also be achieved using inducible promoters, including, but not limited to, the metallothionein IIA promoter and heat shock promoters.

For long-term, high-yield production of recombinant proteins, stable expression is preferred. Rather than using expression vectors which contain viral origins of replication, host cells can be transformed with a cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in enriched media, and then are switched to a selective medium. A number of selection systems may be used, including but not limited to the herpes simplex virus thymidine kinase (Wigler, et al., Cell 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes, which can be employed in tk$^-$, hgprt$^-$ or aprt$^-$ cells respectively. Also, antimetabolite resistance-conferring genes can be used as the basis of selection; for example, the genes for dhfr, which confer resistance to methotrexate (Wigler, et al., Natl. Acad. Sci. USA, 77:3567, 1980; O'Hare, et al., Proc. Natl. Acad. Sci. USA, 78:1527, 1981); gpt, which confers resistance to mycophenolic acid (Mulligan & Berg, Proc. Natl. Acad. Sci. USA, 78:2072, 1981; neo, which confers resistance to the aminoglycoside G418 (Colberre-Garapin, et al., J. Mol. Biol., 150:1, 1981); and hygro, which confers resistance to hygromycin (Santerre, et al., Gene, 30:147, 1984). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:804, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with proteins or peptides according to the present invention. Antibody which consists essentially of pooled monoclonal antibodies with different epitopic specificities, as well as distinct monoclonal antibody preparations, is provided. Monoclonal antibodies are made from antigen containing fragments of the protein by methods well known in the art (Kohler, et al., Nature, 256: 495, 1975; Current Protocols in Molecular Biology, Ausubel, et al., ed., 1989).

Still another aspect of the present invention is a screening method to detect an agent that blocks integrin $\beta_3$ activation. The screening method comprises the steps of:

(1) determining the extent of interaction between the chimeric peptide described above and talin in the presence of an agent to be screened by NMR spectroscopy;

(2) determining the extent of interaction between the chimeric peptide described above and talin in the absence of the agent to be screened by NMR spectroscopy; and (3) comparing the extent of interaction between the chimeric peptide and talin in the presence of the agent and in the absence of the agent to determine whether the agent blocks integrin $\beta_3$ activation.

The agent to be screened can be a protein or a small molecule. If a small molecule, for example, it can be a steroid, an alkaloid, a terpene, a carbohydrate, an amino acid or derivative thereof, a nucleic acid base, a nucleoside, or another small molecule.

Still another aspect of the present invention is a method for screening for alteration in talin function comprising the steps of:

(1) determining the extent of interaction between talin from a subject suspected of having an alteration in talin function and the chimeric peptide described above by NMR spectroscopy; and (2) comparing the extent of interaction found in (1) with the extent of interaction between normal talin and the chimeric peptide as determined by NMR spectroscopy in order to detect or determine the existence of an alteration in talin function.

The invention is illustrated by the following Examples. These Examples are for illustrative purposes only and not intended to limit the invention.

EXAMPLES

Integrins are found throughout the animal kingdom where they play important roles in cell adhesion, migration, proliferation and survival. They are membrane-spanning heterodimers of α and β subunits, both of which typically comprise a short cytoplasmic tail (~20 to 50 residues), a single transmembrane helix and a large extracellular domain (~700 to 1000 residues). In mammals, there are eighteen identified α subunits and eight β subunits that combine to form 24 distinct heterodimers. In humans, integrins play critical roles in development and participate in the pathogenesis of heart disease, chronic inflammation, and cancer (Ginsberg et al., 2005; Hynes, 2002).

Many integrins are expressed with their extracellular domains in a default low-affinity ligand binding state (the 'off state'); however, cells can change the conformation and affinity of these receptors in response to cellular stimulation, a process often termed "integrin activation". This conformational change results in increased adhesion and subsequent signaling, mediating events such as cell migration, platelet aggregation, leukocyte exit from the vasculature and assembly of the extracellular matrix. The binding of a cytoskeletal protein, called talin, to the β subunit cytoplasmic tail is a common final step in the activation process (Tadokoro et al., 2003; Tanentzapf and Brown, 2006).

Talin consists of a large C-terminal rod domain that contains bundles of α-helices and an N-terminal FERM (band four-point-one, ezrin, radixin, moesin) domain with three sub-domains, F1, F2 and F3 (Chishti et al., 1998; Garcia-Alvarez et al., 2003; Papagrigoriou et al., 2004; Rees et al., 1990). Talin colocalizes with integrins (Horwitz et al., 1986) and binds to F-actin and actin-binding proteins (reviewed in (Critchley, 2005)), thus linking the actin cytoskeletal network to the extracellular matrix. The F3 sub-domain of the FERM domain contains the highest affinity integrin binding site for integrin β-tails and is sufficient to activate integrins (Calderwood et al., 2002). A partial view of this interaction was obtained in a crystal structure of the F2 and F3 domains of the talin FERM domain in complex with a 12 residue fragment ($^{739}$WDTANNPLYDEA$^{750}$) (SEQ ID NO: 1) comprising ~25% of the β3 integrin tail (Garcia-Alvarez et al., 2003). That work confirmed that the F3 domain has a phosphotyrosine binding (PTB) domain fold and that its interaction with integrins strongly resembles the interaction of other PTB domains with peptide ligands (Garcia-Alvarez et al., 2003). Several other PTB domains bind to β3 in a similar fashion to talin (Calderwood et al., 2003; Garcia-Alvarez et al., 2003) but only talin has exhibited the capacity to activate integrins. Thus, we reasoned that additional unique features of the integrin/talin interaction enable talin to cause activation. Indeed, NMR spectroscopic evidence had suggested an interaction between talin F3 and the membrane-proximal (MP) region of the β-tail (Ulmer et al., 2003; Vinogradova et al., 2002) that is important for activation (Hughes et al., 1995; Ulmer et al., 2003). However, such an interaction has not been directly observed.

Here, we provide the first atomic level description of the interaction between talin and the MP region of the β3-integrin cytoplasmic domain. Structure-based mutagenesis shows that disruption of the newly identified interactions blocks integrin activation in cells while retaining binding to the membrane-distal (MD) region of β3. These results define the talin/integrin interactions that lead to integrin activation and explain why talin is unique among PTB-containing proteins in its activating ability. They also identify an interaction that is a target for the rational design of therapeutics that block integrin activation; the new understanding also allows the engineering of cells or animals with selective defects in integrin activation.

Example I

Talin Interacts with Both the Membrane-Proximal and Membrane-Distal Regions of the β3-Tail We set out to obtain a structural explanation for the unusual ability of the talin PTB domain to activate integrins. An initial exploration of the interactions was carried out by adding various tail-derived β3-integrin peptides to the F3 sub-domain of talin, while monitoring the chemical shift perturbations in $^1$H-$^{15}$N HSQC NMR spectra. The peptide sequences and the nomenclature used are set out in FIG. 1A. The MP peptide corresponds to the N-terminal region of the cytoplasmic β-tail. A peptide comprised of the β-tail region previously visualized in the crystal structure (Garcia-Alvarez et al., 2003), is denoted MD; this peptide primarily causes chemical shift perturbations in strand S5 (de Pereda et al., 2005).

The chemical shifts for the MP peptide show that it interacts with a site on F3 that is distinct from the MD binding site (FIG. 1). The new perturbations found in the MP-binding site mainly arise in residues that form a loop between the first and second beta strands (S1 and S2) of the F3 structure. Residues 358 and 359 of F3 are also perturbed, presumably due to the β-tail residue W739 which is included in both the MP and MD peptides and binds tightly in a pocket on the surface of F3.

Figure 8:
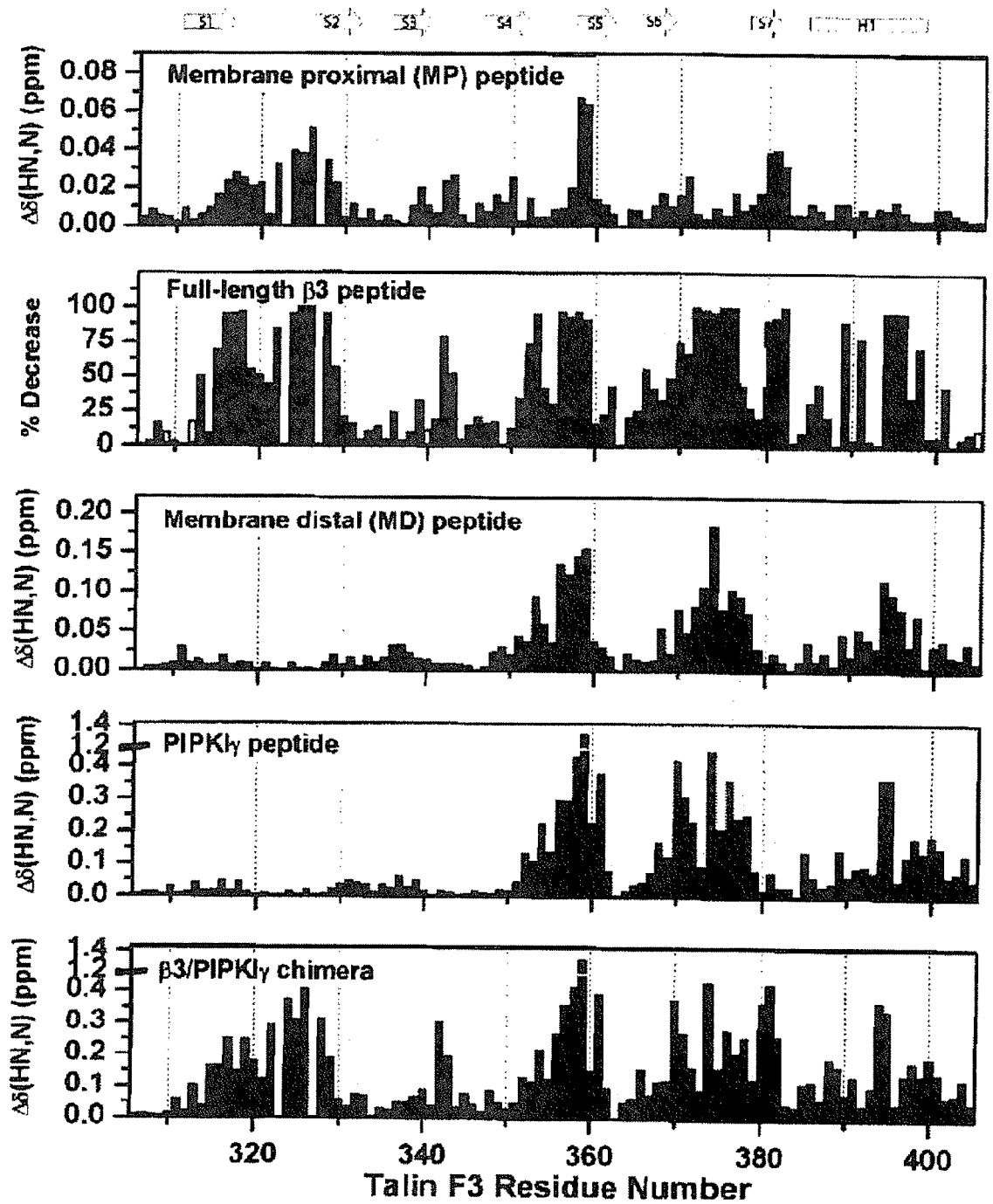
FIGS. 8-12 are supplementary data showing the structural basis of integrin activation by talin.

NMR studies of the interaction with full-length β3 cytoplasmic tail were more challenging. The off-rates of the complex correspond to an 'intermediate exchange' regime, with peaks broadening and disappearing rather than changing position. It was, however, possible to define perturbed residues by plotting the percentage decrease in peak height upon addition of the peptide (FIGS. 1D and 8). The perturbed residues are essentially the sum of those affected by the MD peptide and the MP peptide (FIGS. 1 and 8). The β3 tail/talin F3 interactions can thus be considered in two parts, one corresponding to the previously defined interaction at the MD-site, the other corresponding to the MP-site. The limited solubility of the full-length β3 tail meant that it was not possible to produce a 1:1 complex at the concentrations used. This, together with exchange broadening of lines, made the β3 tail an unsuitable ligand for studying the structure of the talin-integrin complex by NMR at atomic resolution.

We have, however, previously shown that a peptide segment from phosphatidylinositol phosphate kinase type Iγ (PIPKIγ) binds in a similar manner to the β3 integrin peptide in the MD site (de Pereda et al., 2005). These data are shown again here for comparison (FIGS. 1D and 8). Both peptides bind to talin F3 and form a β-strand followed by a reverse turn, but the PIPKIγ peptide binds with much higher affinity in a slow-exchange NMR regime, and a 1:1 complex is readily achieved. Critically, W739 from the β3 tail and W642 from the PIPKIγ peptide occupy essentially identical positions and adopt identical main-chain and side-chain torsion angles, each binding in a deep pocket on the talin protein surface (de Pereda et al., 2005; Garcia-Alvarez et al., 2003). This strong similarity led us to believe that a synthetic chimeric peptide, comprised of β3 integrin tail residues on the N-terminal side of the critical tryptophan and PIPKIγ residues on the C-terminal side, would yield a peptide ligand with higher affinity and better solubility, suitable for high resolution studies of the F3-MP interaction. The sequence of the designed chimeric peptide is shown in FIG. 1A. NMR experiments showed that this chimeric peptide does indeed bind to talin and form a tight, highly soluble 1:1 complex. Moreover, comparison of the protein backbone chemical shifts in the bound and unbound states indicates that the residues affected by the chimeric peptide are essentially the sum of residues affected by the MP integrin peptide and those affected by the PIPKIγ peptide (FIGS. 1 and 8), supporting the idea that the chimera is suitable for structural studies of the F3-MP interaction.

Example II

Figure 2:
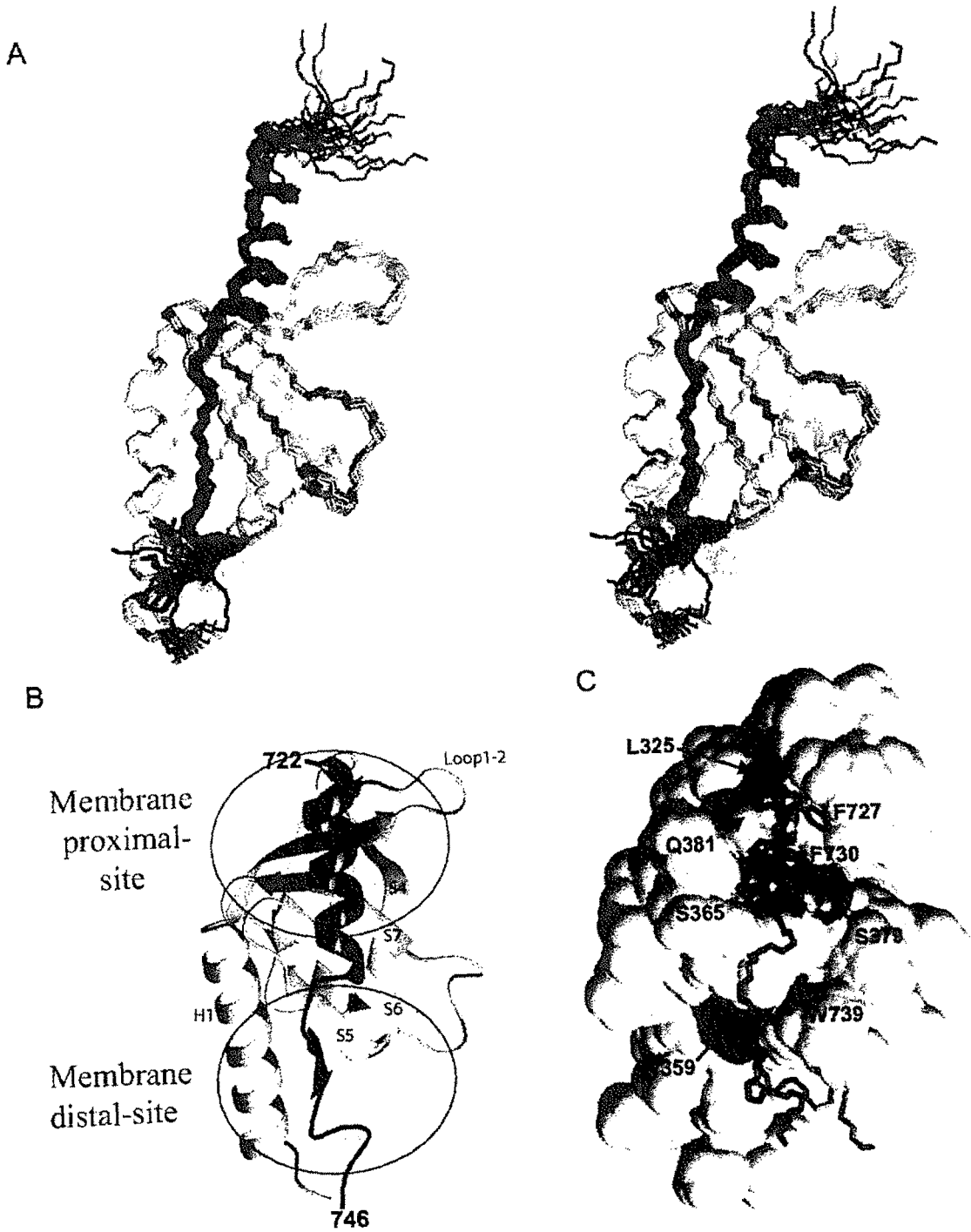
FIG. 2 shows the structure of the talin F3-chimeric peptide complex. A. Stereo view of 20 calculated structures, superimposed along the well-ordered residues of the talin F3 domain ($^{15}$N-$^1$H-NOEs>0.65). B. Ribbon representation of the complex showing the approximate location of the MD and MP binding sites. C. The talin F3 domain is shown in white as an accessible surface representation, with residues that were mutated for subsequent experiments indicated in color—L325 (green), W359 (pink), S365 (purple), S379 (blue) and Q381 (yellow). The chimeric peptide backbone (residues 723-746), as well as the side-chains of the two phenylalanine residues (F727 and F730), are shown in red. Overlaid on the complex structure in cyan is the position of the β$_3$-integrin tail fragment found in the crystal structure 1MK7 (Garcia-Alvarez et al., 2003). The critical tryptophan (W739) side-chains from the crystal structure and the NMR structure are also shown.

The Structure of the Talin F3/Peptide Complex Reveals a Binding Interface with the MP-Site The structure of the complex was calculated from NMR data using a total of 2187 experimental restraints, 138 of which were unambiguous intermolecular NOEs (Table 1, FIG. 2). As expected, the PIPKIγ-derived portion of the peptide binds in a very similar manner to that seen in the crystal structure (de Pereda et al., 2005); the SPLH sequence (residues 742-745) forms a reverse turn and residues 739-741 create a β-strand that augments the β-sheet formed by strands S5-S7 from talin (FIG. 2). Importantly, the pivotal tryptophan residue (W739) that connects the two sequences in the chimera aligns closely with the same residue in the crystal structure of the β3 tail complex (Garcia-Alvarez et al., 2003) (FIG. 2C). This strongly suggests that residues 716-739 of the β3 tail are free to adopt their native orientation in the F3 complex. The extended nature of the complex and the relative rigidity of the F3 domain are consistent with the notion that the MD-site and the MP-site behave relatively independently (FIG. 2B). Thus any differences between the native integrin peptide and the chimeric peptide are restricted to the MD site. The structural and functional implications of differences between the binding of the PIPKIγ peptide and the β-tail MD site have been discussed previously (de Pereda et al., 2005).

Figure 9:
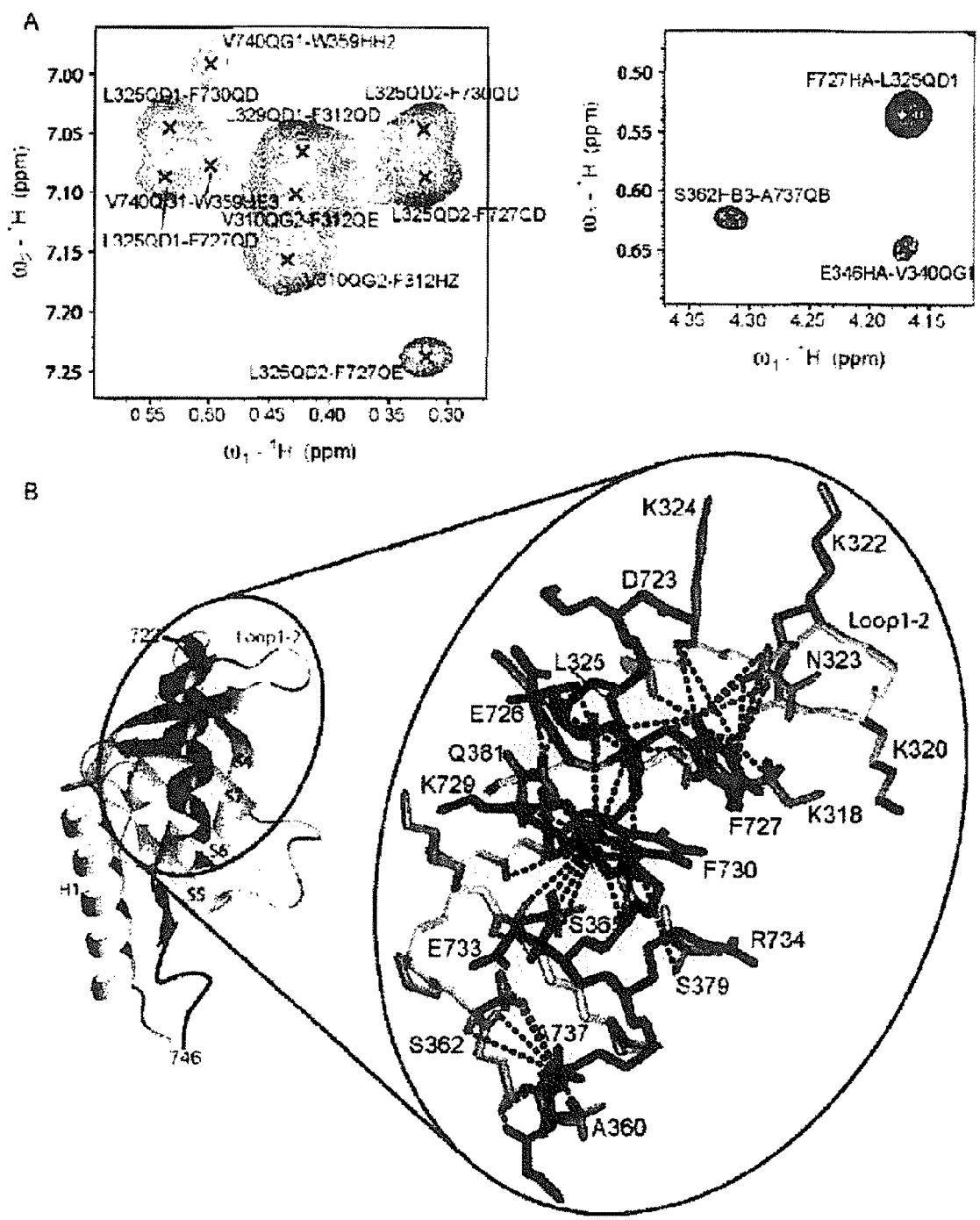

The new structure reveals important novel contacts between the MP region of β3 and talin. Specifically, the β3-derived portion of the peptide forms an α-helix between H722 and R736. This helix lies across strands S1-2 and S6-7 of the talin F3 domain, burying two phenylalanine residues of the $β_3$ tail (F727 and F730). Of the 138 intermolecular NOEs used in the structure calculation, 57 define the MP integrin/talin interface. The majority of these involve the two phenylalanine residues F727 (23 NOEs) and F730 (18 NOEs). The hydrophobic talin residue L325 appears important for this interaction and 7 NOEs were identified between this residue and these phenylalanine side-chains (See FIG. 9). The calculated structure is consistent with the chemical shift changes in the F3 domain observed during NMR titration experiments (FIG. 8).

Figure 10:
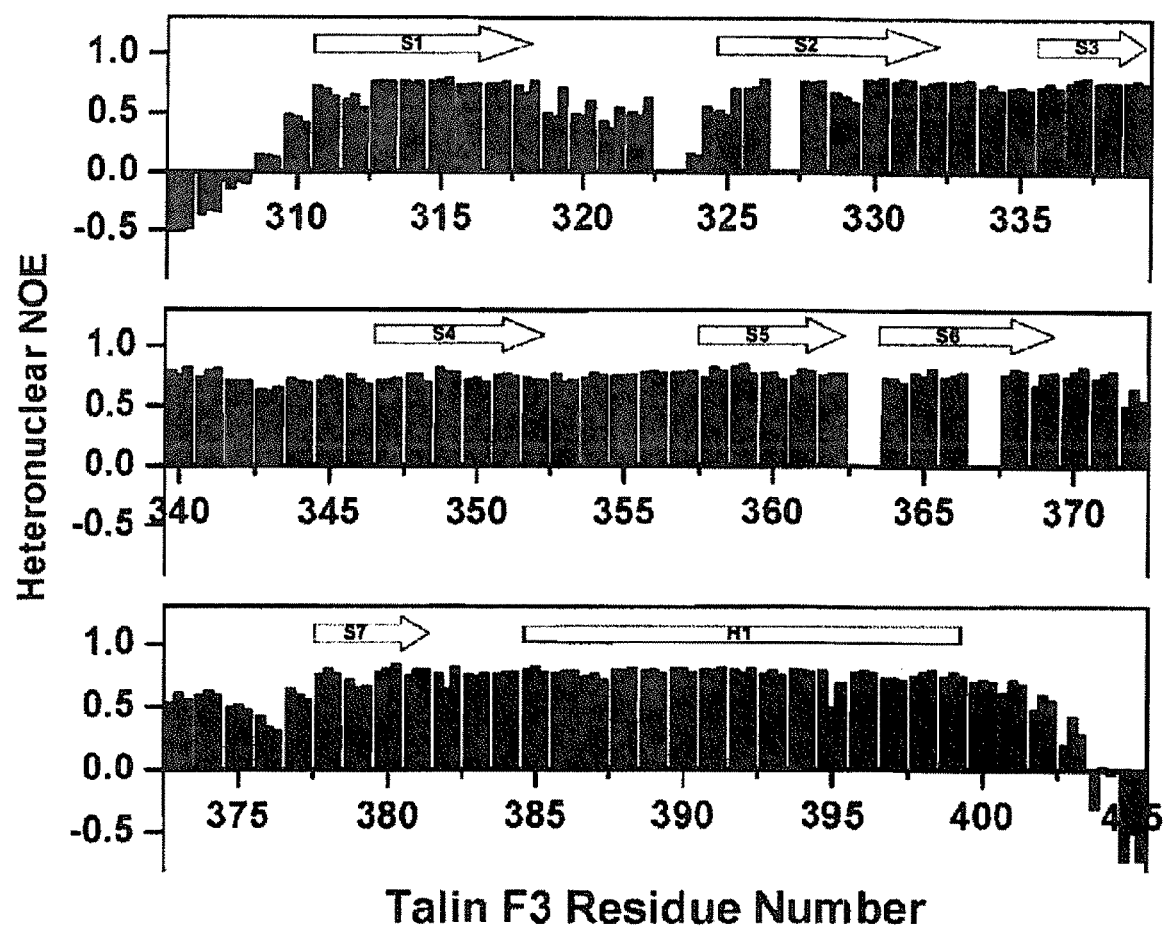

There is a propensity for residues 722-732 of the free β3 peptide to form an α-helical structure, since the α-proton chemical shifts of these residues are consistently downfield from random coil values. Binding to the talin F3 domain further increases the downfield shifts of these β-tail resonances, indicating that the helix is stabilized in the complex (data not shown). Heteronuclear $^1H$-$^{15}N$ NOEs were recorded for the protein alone as well as in complex with various peptides (FIG. 10). The results indicate that the loop between S1 and S2 of talin F3 is stiffened by binding to the MP region of the β3 tail, which again supports the calculated structure.

Example III

Mutation of β-Membrane Proximal Residues that Contact F3 Diminish the Ability of Talin to Activate Integrin αIIbβ3

Contacts between talin and the MP region of the β3 cytoplasmic tail may constitute an interaction that is a key to the activation process. To test this concept, the effects of a number of designed mutations, both in the β3 tail and in the talin F3 sub-domain, were investigated. Integrin activation was assessed using the antibody PAC1 and flow cytometry as previously described (Partridge et al., 2005).

Figure 3:
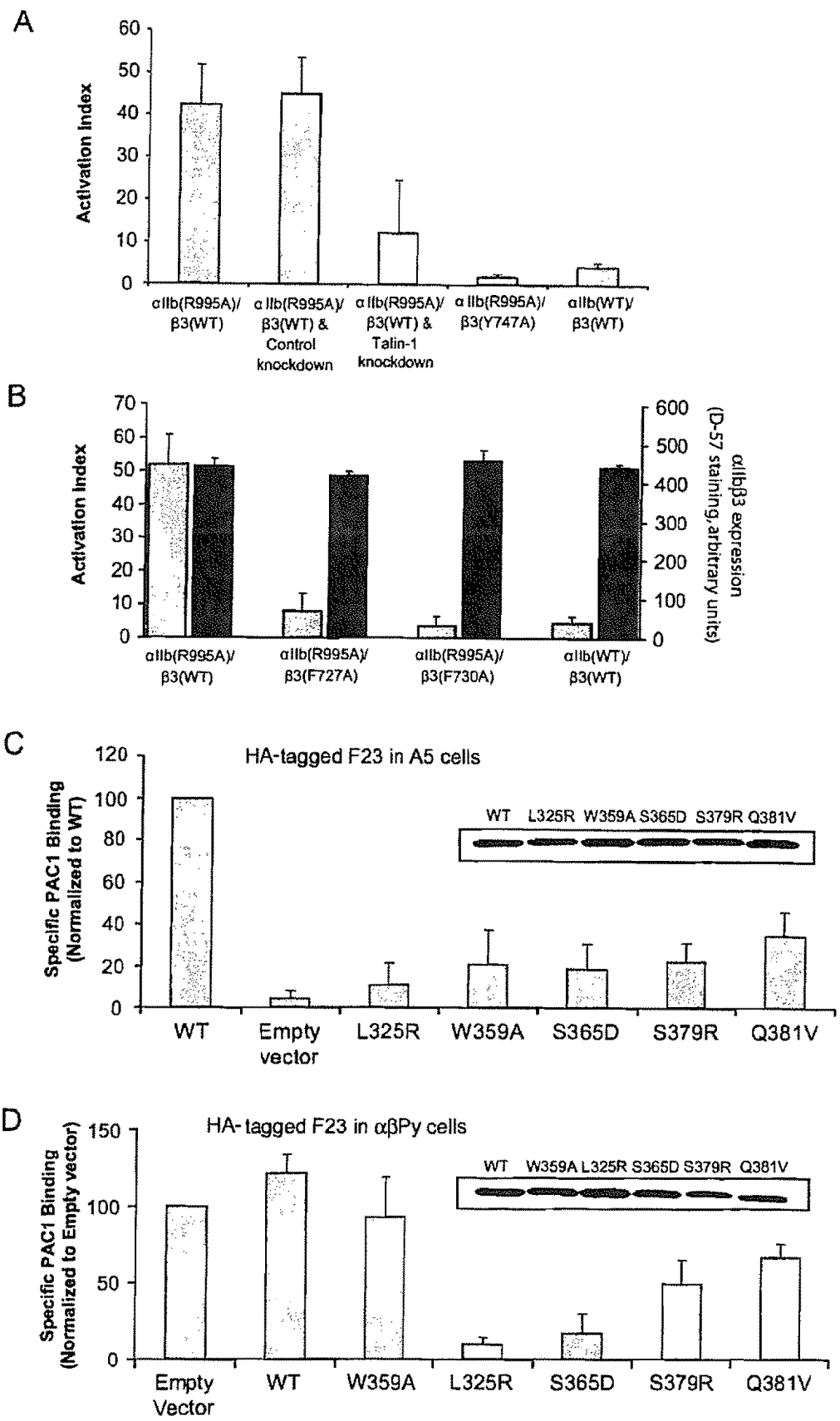
FIG. 3 shows that talin mediated integrin activation requires specific contacts between the β3 membrane-proximal region and talin F3. A-B. CHO cells were transiently transfected with plasmids encoding αIIb and β3, or mutants thereof. In some samples (indicated above) a plasmid encoding a shRNA for talin-1 (Tadokoro et. al. 2003) or a control shRNA was co-transfected with the integrin plasmids. Cells were double stained for integrin αIIbβ3 expression (B-D57) and activated αIIbβ3 (PAC1) and flow cytometry was used to measure the geometric mean fluorescence intensity (F) of PAC1 binding. Non-specific PAC1 binding (F0) was measured in the presence of a competitive antagonist of αIIbβ3, Ro43-5054 and maximal binding (Fmax) was measured in the presence of the activating antibody Anti-LIBS6. Activation index was defined as 100*(F−F0)/(Fmax−F0) (see Experimental Procedures). A. Activation of αIIb(R995A)β3 integrin was diminished in the cells co-transfected with talin-1 knockdown shRNA. Similarly, the β3(Y747A) mutation blocks talin binding to the MD site and the αIIb(R995A) β3(Y747A) integrin is not activated. B. Talin-mediated activation requires specific contacts between talin F3 and the β3 MP region. Depicted is the Activation Index (gray bars) or the αIIbβ3 expression, indicated as fluorescence intensity of D57 staining (black bars). The activating effect of αIIb(R995A) is diminished when it is paired with the β3 MP mutants β3(F727A) or β3(F730A). C-D. CHO cells stably expressing WT human αIIbβ3 (A5 cells), or a high-affinity chimeric integrin (αβPy cells), were transiently co-transfected with vectors for WT or mutant HA-tagged talin F23 and eGFP protein as a transfection marker. PAC1 binding was measured by flow cytometry in the subset of cells expressing GFP. Insets show representative western blots of cell lysates probed with anti-HA antibody and indicate that WT and mutant HA-talin F23 expressed to similar levels. C. Specific PAC1 binding in αIIbβ3-expressing A5 cells transfected with talin F23 mutants relative to that in cells transfected with wild type talinF23 (set as 100). Mutants to MP contacting residues (L325R, S365D, S379R, Q381V) and MD contacting residues (W359A) prevent activation. D. PAC1 binding in αIIbα6β3β1-expressing αβPy cells transfected with talin F23 or its mutants relative to that in cells transfected with empty vector (set as 100). The MP-contacting talin F23 mutants (L325R, S365D, S379R, Q381V) inhibited activation, whereas the MD-contacting mutant talin F23(W359A) had no significant effect on activation levels. All data are an average of three of more measurements, error bars are standard deviations.

The effects of mutating F727 and F730, which make intimate contact with F3, were investigated using a mutant integrin αIIb subunit, R995A. When paired with a wild type β3 subunit the assembled integrin is in an activated state (FIG. 3A), consistent with previous reports (Hughes et al., 1996). The activated state is dependent on endogenous talin, as shown by the decrease or abolition of ligand binding when the influence of talin is reduced, either by talin knock-down or by a mutation in the β-tail (Y747A) that disrupts talin binding (Tadokoro et al., 2003) (FIG. 3A). When αIIb(R995A) was paired with β3 mutants designed to disrupt the F3/MP interaction, β3(F727A) or β3(F730A), the activating effect of the αIIb(R995A) mutation was dramatically reduced (FIG. 3B).

Example IV

Mutation of F3 Residues that Contact the β-Tail Diminish the Ability of Talin to Activate Integrin αIIbβ3

Figure 4:
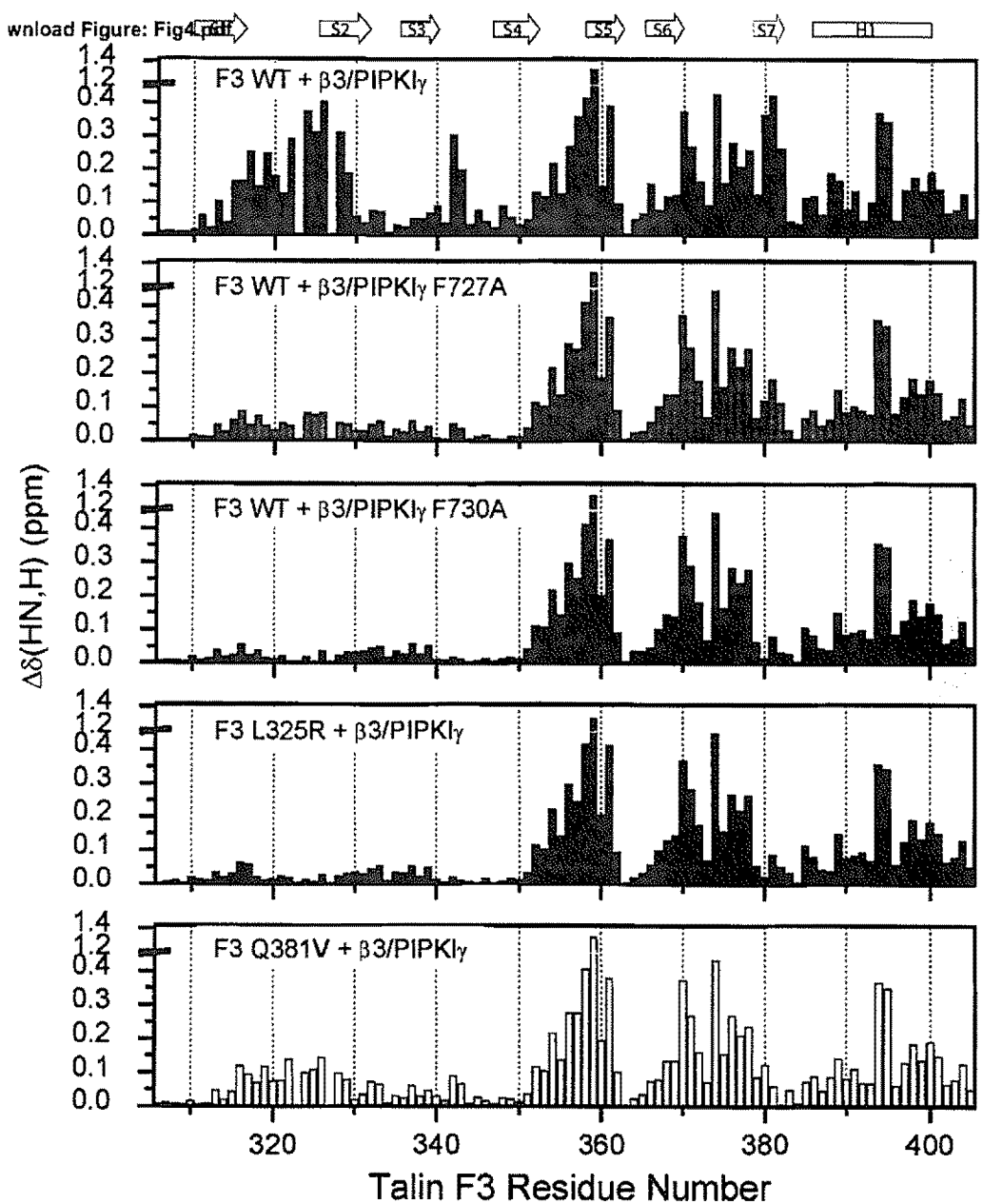
FIG. 4 shows weighted shift maps (see Experimental Procedures) obtained by observing $^1$H-$^{15}$N HSQC spectra of talin F3 constructs on addition of β3/PIPKIγ peptides. Talin F3 L325R and Q381V mutants were titrated with the original β3/PIPKIγ chimera, while the effect of peptide mutations (F727A and F730A) was assessed using wild-type talin F3. The shift maps indicate that binding to the MP region (via the talin loop between S1 and S2) is markedly reduced for the Q381V and F727A mutants, or completely abolished for the L325R and F730A mutants, while interactions with the MD region are retained.
Figure 11:
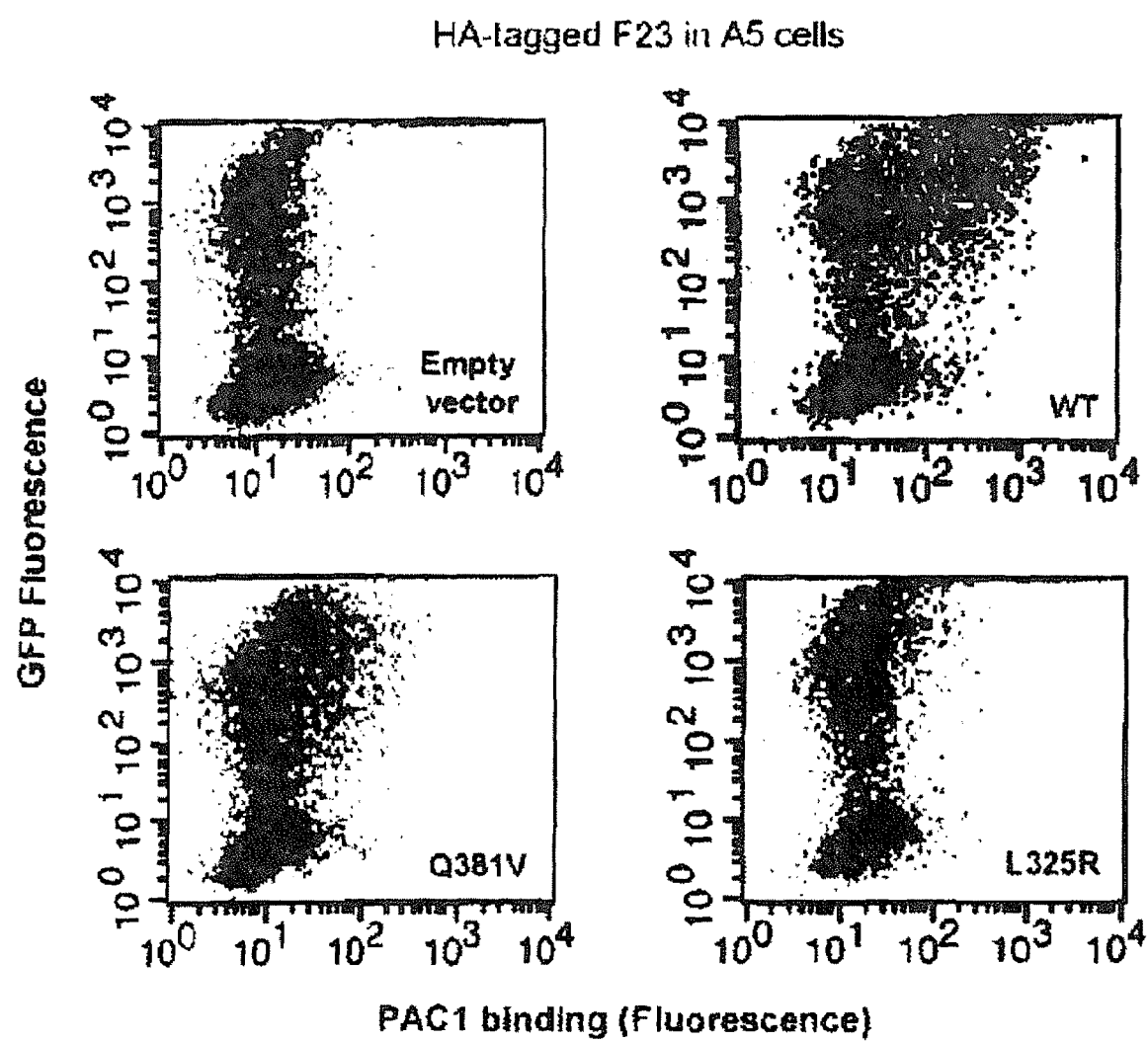

Mutations to the contact residues in talin F3 (L325R, S365D, S379R, or Q381V) were also made to see if they disrupted the F3/MP interaction. Mutants were correctly folded as judged by their dispersed NMR spectra (data not shown), and chemical shifts induced by addition of chimeric peptide indicated that binding to the MD site was unchanged. In contrast, perturbation of contact residues in the MP region was either markedly reduced (F3-Q381V and β3-F727A) or undetectable (F3-L325R and β3-F730A) (FIG. 4). Transfection of cells with cDNA encoding the F2 and F3 sub-domains (F23) of talin (residues 206-405) is known to activate several integrins (Calderwood et al., 2002) but each of the four mutations diminished the ability of F23 to activate integrin αIIbβ3 (FIGS. 3C and 11). These results establish the biological relevance of the interactions seen between the talin F3 protein and the MP region and show that these interactions are critical for integrin activation.

Example V

Talin Mutants that Inhibit Integrin Activation

The observation that talin mutants with impaired contacts to the MP region still bind to the chimeric peptide via the MD-site suggested that they might compete with and displace endogenous talin, thus inhibiting integrin activation. To investigate this possibility we used αβPy cells, a CHO cell-line expressing a talin-dependent constitutively active chimeric integrin composed of the extracellular and transmembrane domains of αIIbβ3 and the cytoplasmic tails of α6β1 (Baker et al., 1997). We transiently transfected αβPy cells with cDNAs encoding the mutant F23 constructs (L325R, S365D, S379R, or Q381V). Each of the four mutants blocked integrin activation (FIG. 3D), a result consistent with competition between endogenous full-length talin and the activation-defective F23 mutants for binding to the β MD site. In contrast, transfection of these cells with cDNA encoding wild type F23 modestly increased activation whereas a mutant that strongly inhibits the MD binding site, F23(W359A), had no effect on activation, consistent with its markedly reduced affinity for the β tail (Table 2).

To assess whether other PTB domains could recapitulate the dominant negative effect of the talin mutants, αβPy cells were transfected with the PTB-containing protein DOK1. As predicted, this protein inhibited integrin activation (FIG. 5A), consistent with the idea that it competes with endogenous talin for the MD-site, but does not induce activation. Comparison of the structures of the DOK1 and talin PTB domains shows that they differ primarily in the region between strands S1 and S2 (FIG. 5B), consistent with the idea that this region is vital for activation. Titration of the DOK1 PTB domain with the β3/PIPKIγ peptide revealed interactions with S5, S6 and H2, indicative of binding to the MD region, whereas no interactions with the S1 to S2 region were observed (FIG. 5C). These results explain the unique ability of talin to activate integrins and provide a structural explanation for the capacity of certain other PTB domain-containing proteins (Huang et al., 2004) to inhibit integrin function.

Figure 12:
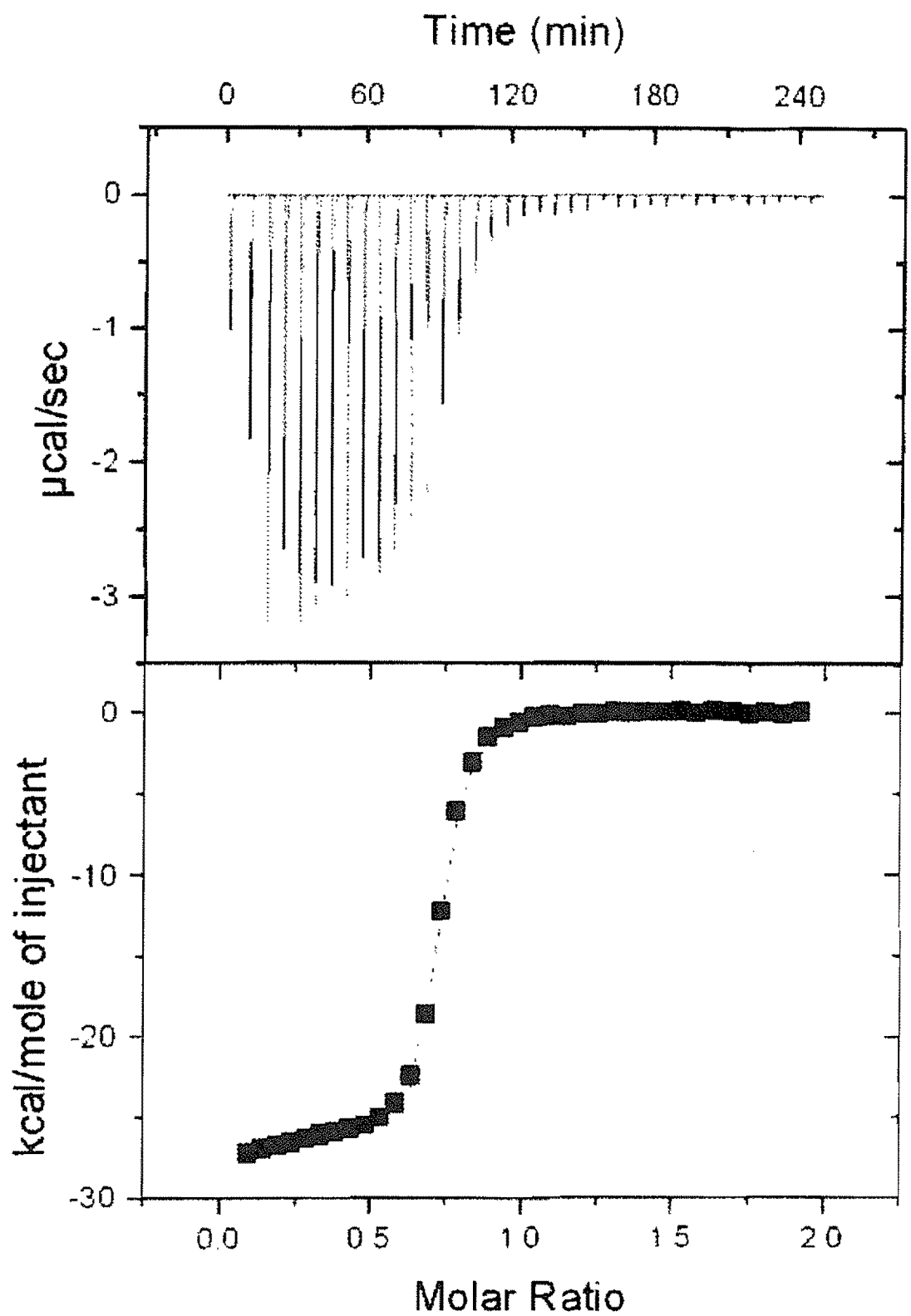

Thermodynamic parameters for the binding of WT and mutant talin F3 to the β3 chimeric peptides were measured using isothermal titration calorimetry (Table 2, FIG. 12). In general, mutations that disrupt the MP site, either in the β-tail or talin F3, have relatively little effect on the Kd values (Table 2). This probably arises because of a balance between enthalpy gain and entropy loss, consistent with stabilization of the MP helix on talin binding in the wild-type but not mutant structures. In sharp contrast, the talin (W359A) mutant, which inhibits binding of the MD-site of the β3 tail, reduced the affinity ~1000 fold, similar to the effect of mutations in the NPxY region of the integrin tail, which abrogate MD binding (Ulmer et al., 2003). These results suggest that the MD-site provides a substantial fraction of the binding energy and explains why other PTB domains, which only bind the MD-site, could readily compete with talin.

Example VI

An Activating Mutant in the Transmembrane Domain is Talin-Independent

Figure 6:
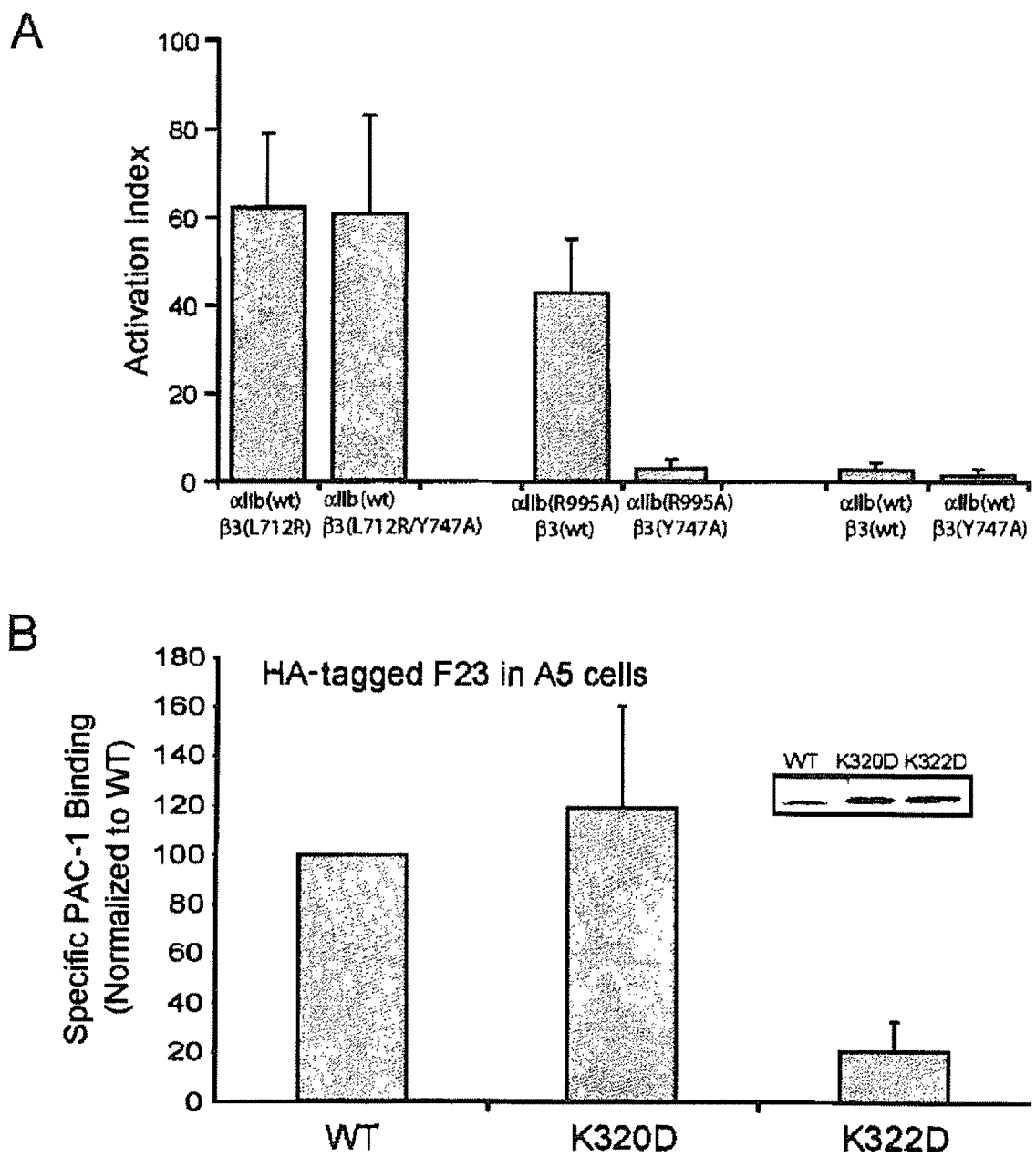
FIG. 6 shows the effect of a transmembrane (TM) integrin mutation, and talin S1-S2 loop lysine mutations, on integrin activation. A. CHO cells were transiently transfected with plasmids encoding αIIb and β3, or mutants thereof, and the cells were double stained with PAC1 and D57 to measure integrin activation and αIIbβ3 expression respectively. Integrin activation was estimated as described in the legend to FIG. 3. Both the putative TM-shortening mutation β3(L712R) and the salt-bridge breaking αIIb(R995A) mutation result in an activated integrin. However, when paired with a mutation that disrupts talin binding to form αIIb (R995A)β3(Y747A), the R995A mutation loses the ability to induce the high-affinity state whereas the β3(L712R) mutation's activation level is unchanged in the αIIbβ3(L712R, Y747A) integrin. B. CHO cells stably expressing αIIbβ3 (A5 cells) were transiently co-transfected with vectors for WT or mutant HA-tagged talin F23 and eGFP protein as a transfection marker and PAC1 binding was assessed in the GFP-expressing subset of cells by flow cytometry and analyzed as described in the legend to FIG. 3. Mutation of lysine K320 (K320D), which is predicted to point away from the membrane, had no effect on activation, while mutation of K322 (K322D), a residue which is directed toward the membrane, prevented activation. The inset to B shows representative western blots of cell lysates probed with anti-HA antibody and indicate that WT and mutant HA-talin F23 expressed to similar levels. The data are an average of three of more measurements, error bars are standard errors of the mean.

We previously proposed that talin binding to the β-subunit cytoplasmic domain results in a mismatch in the packing of the transmembrane regions of α and β subunits (Partridge et al., 2005). Modeling and mutational approaches indicate that interactions between the transmembrane regions stabilize the integrin low affinity state (Bennett, 2005; Gottschalk, 2005; Luo et al., 2005; Partridge et al., 2005). Another interaction that helps maintain the inactive conformation is the αIIb (R995)/β3(D723) MP salt-bridge (Hughes et al., 1996). We note, however, that breaking this link, while shifting the equilibrium towards the active state, does not promote full activation, which requires endogenous talin (Tadokoro et al. 2003). To test if transmembrane mutations activate in a talin-independent manner, the apolar-to-charged mutation β3(L712R) was analyzed. A combination of this mutant with β3(Y747A), a mutation that prevents binding to the talin F3 MD-site, αIIbβ3(L712R,Y747A) remained fully activated (FIG. 6A), confirming that disruption of transmembrane helix packing activates integrin αIIbβ3 independent of talin binding.

A combination of NMR studies, together with cell-based functional assays, has revealed how the talin F3 domain is uniquely designed to activate integrins. The talin F3 domain forms a well-defined complex with the helix-forming MP region of the β-integrin tail and this interaction holds the key to the molecular recognition required for activation. Mutations in integrin or talin that inhibit this interaction in vitro also prevent integrin activation in cells, and mutants with intermediate functional effects in cells retain a partial ability to form the F3/MP interaction (compare FIGS. 3 and 4). These findings are consistent with previous studies that identified a variety of activating mutations within the MP region of integrins, establishing that this region is critical for stabilizing the low affinity conformation (Ginsberg et al., 2005; Partridge et al., 2005).

Figure 5:
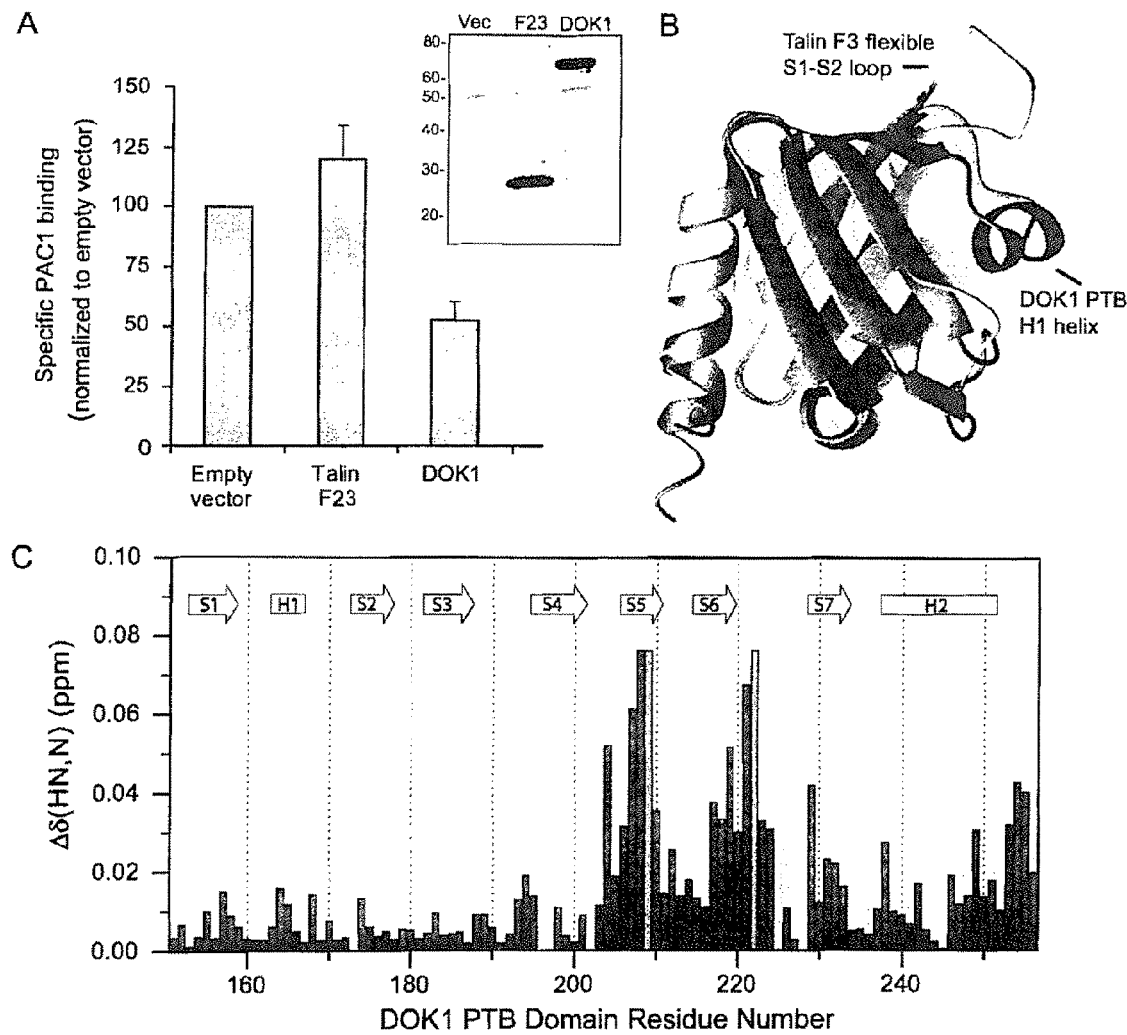
FIG. 5 shows that β-tail binding to the DOK1 PTB domain inhibits activation of a high-affinity integrin. A. CHO cells stably expressing a high-affinity chimeric integrin (αβPy cells) were transiently co-transfected with empty vector (pCDNA3.1), WT talin F23 or full-length DOK1; eGFP protein was used as a transfection marker. The level of integrin activation was measured by flow cytometry of harvested cells using PAC1 antibody as described in the legend to FIG. 3. Data are an average of three or more measurements; error bars are standard deviations. B. Overlay of the DOK and talin PTB domains. The critical differences between the two domains are the residues between strands S1 and S2. C. Weighted shift map (see Experimental Procedures) obtained by observing $^1$H-$^{15}$N HSQC spectra on addition of the β3/PIPKIα peptide to the DOK PTB domain (10:1 molar ratio). Grey columns indicate residues whose peaks experienced severe line broadening in the bound state and could not be assigned.

The unique feature of talin F3 that promotes interaction with the MP region of β-integrin appears to be the flexible loop between strands S1 and S2, which forms a hydrophobic pocket that accepts the side chains of F727 and F730 in the complex. The talin mutation L325R within this pocket abolishes binding to the MP region (FIG. 4) and thus hinders activation (FIG. 3C). Other PTB domain-containing proteins—DOK ('IRS-like'), Shc ('Shc-like') and NUMB ('Dab-like') (Uhlik et al., 2005)—lack such a mobile loop and so are unlikely to interact with the MP region (FIG. 5B). Indeed, we showed that DOK binds and inhibits integrin activation and that binding occurs to the MD but not the MP site (FIG. 5). Several point mutants in talin also transform the F3 domain from an activator into an inhibitor (FIG. 3D). This is consistent with competition between endogenous talin and various PTB domains, including mutated talin F3, for the MD-site The concept of inhibition of talin activation by competitive binding to the β-tails by a variety of proteins, especially those with PTB domains, may be an important feature in the regulation of integrin activity. These conclusions also apply to PTB (F3) sub-domains in other FERM domain proteins. The FERM domain structures of band 4.1, ezrin, radixin and moesin all have very short loops between strands 1 and 2 with no hydrophobic residues that could bury the two integrin phenylalanines (Edwards and Keep, 2001; Hamada et al., 2000; Han et al., 2000; Smith et al., 2003).

Integrin activation is critical for a variety of pathological events such as thrombosis, inflammation, and tumor metastasis (Campbell and Ginsberg, 2004). The interface between the MP region of β3 and talin suggests that it might be readily accessible to pharmacological inhibition. In particular, the two critical β3 phenylalanines (F727 and F730) are 6 angstroms apart along the same helical face and are accommodated in a relatively discrete binding pocket. Thus, molecular docking approaches should enable the design of compounds that occupy this binding pocket thus blocking the MP interaction. Further, since the MP interaction makes little contribution to the affinity of talin-integrin binding, disrupting the interaction pharmacologically or by mutation should provide tools to selectively disrupt talin-mediated integrin activation for experimental or therapeutic purposes.

How does the talin/MP interaction lead to activation? One possibility is that the configuration of the complex disrupts the putative salt bridge between αIIb(R995) and β3(D723). Several distinct models for the α-β tail complex have been published, and the F3-MP complex would sterically prevent the formation of the salt bridge in some of these (Gottschalk, 2005; Vinogradova et al., 2002; Weljie et al., 2002) (Table 3). We note, however, that while breaking this salt bridge seems to be necessary, it is not sufficient for full activation (FIG. 3A) (Tadokoro et al., 2003). Prevention of β3 binding to the MD-site by the β3(Y747A) mutation also inhibits activation of the αIIb(R995A)β3 (FIG. 3) and β3(D723R) forms of integrin (data not shown). Talin binding to the MD-site might contribute to activation by displacing this part of the integrin tail from a membrane-anchored position (Vinogradova et al., 2004); however, it is hard to reconcile this idea with the inactive state of the αIIb(R995A)β32(F727A) or αIIb (R995A)β3(F730A) integrins (FIG. 3B) in spite of destabilization of the salt bridge and talin still binding via the MD-site. In contrast, our data suggests that the primary function of the talin/MD interaction is to provide an initial strong linkage between talin and integrin and that activation arises from the subsequent talin/MP interaction.

We have proposed that activation involves disruption of transmembrane helix interactions (Partridge et al., 2005). A related model with the additional possibility of homo- and hetero-dimeric interactions has been proposed by Li et al. (Li et al., 2005), and interactions between membrane-spanning regions have also been modeled (Gottschalk, 2005), and implied by leucine mutagenesis (Luo et al., 2005). Glycosylation mapping was used to explore whether the membrane spanning regions changed positions in the membrane (Stefansson et al., 2004). Here we made a mutation in the membrane spanning region, β3(L712R), which is expected to reposition the trans-membrane helix, allowing the arginine guanidinium group to snorkel out of the bilayer into a more hydrophilic environment. The activating—yet talin independent—property of β3(L712R) (FIG. 6) is consistent with integrin activation involving repositioning of the β transmembrane helix. Since, in the absence of other proteins, integrins are in equilibrium between the inactive and active states, one possibility is that the β-integrin subunit transmembrane domain is dynamic, bobbing in and out of the membrane, with its transmembrane helices sampling various degrees of burial within the bilayer. Formation of a stable MP β3 helix in intimate contact with talin F3 would promote a conformation in which transmembrane domain residues are further out of the membrane than in the 'off state', pushing the equilibrium towards the active conformation.

Figure 7:
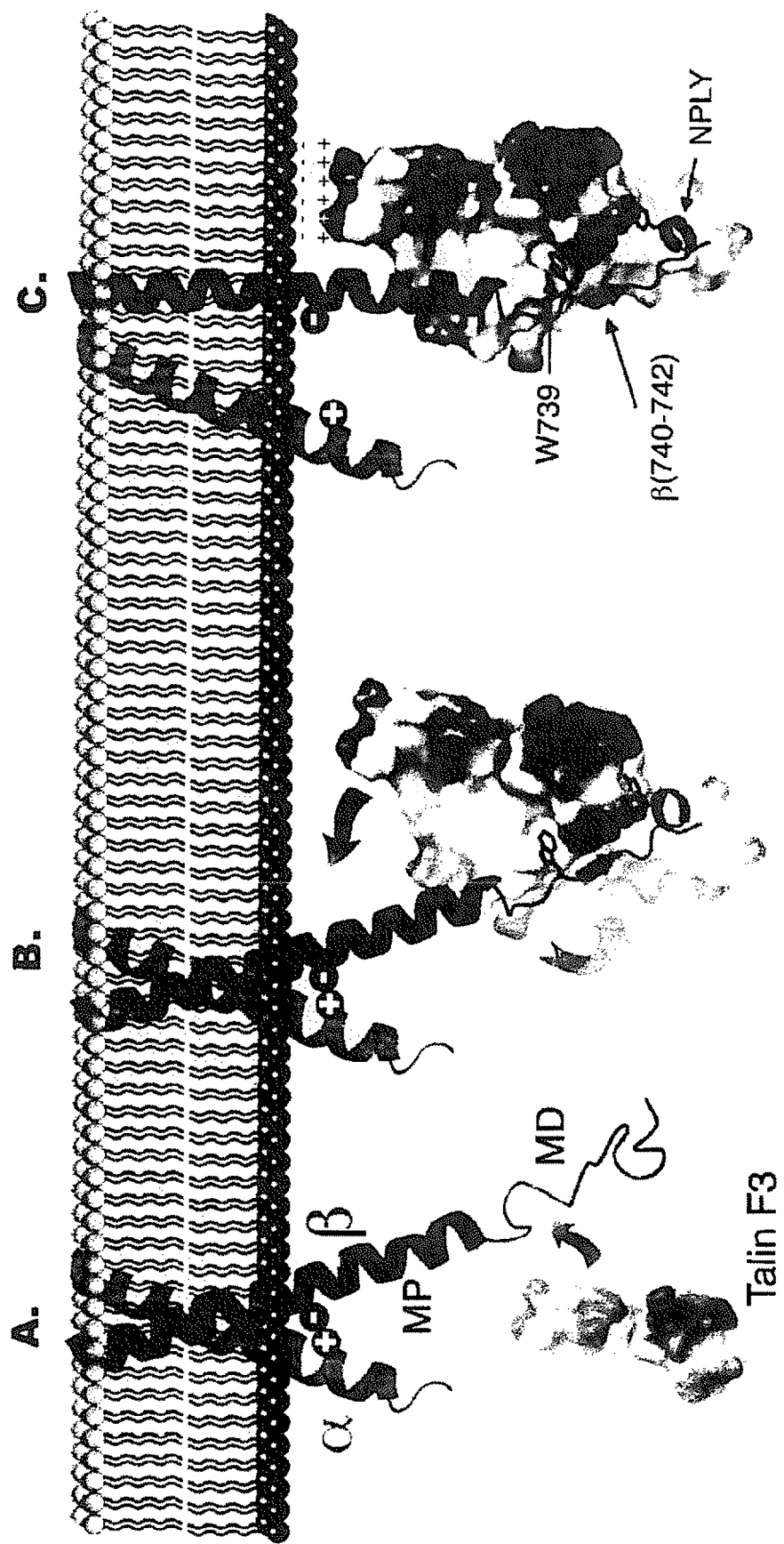
FIG. 7 is a model of talin-induced integrin activation. A. The talin F3 domain (surface representation, colored by charge), freed from its autoinhibitory interactions in the full-length protein, becomes available for binding to the integrin. B. F3 engages the MD part of the β3-integrin tail (in red), which becomes ordered, but the α-β integrin interactions that hold the integrin in the low affinity conformation remain intact. C. In a subsequent step, F3 engages the MP portion of the β3-tail while maintaining its MD interactions. Consequences of this additional interaction are: 1) destabilization of the putative integrin salt-bridge; 2) stabilization of the helical structure of the MP region and 3) electrostatic interactions between F3 and the acidic lipid head-groups. The net result is a change in the position of the transmembrane helix, which is continuous with the MP β-tail helix, causing a packing mismatch with the αIIb transmembrane helix, separation or reorientation of the integrin tails and activation. Mutants of F3 that have compromised interactions with the MP region and other PTB domains that lack an MP binding site, stall at point B, consistent with their dominant negative behavior.

The structure-function analysis reported here provides a cogent structural model to explain talin-dependent integrin activation (FIG. 7). When the F3 domain engages the β-MP region, additional favorable electrostatic contacts between F3 and the lipid head groups can be made. For example, two lysine residues (316 and 322) within the large S1-S2 loop, which contacts the N-terminal end of the β-MP helix, would point towards the acidic head groups of the membrane bilayer. K343 and K345 from the flanking loop, also contribute to making the membrane proximal surface of talin F3 highly basic. When the β-MP and transmembrane regions are modeled as a continuous α-helix and the F3 lysines brought into apposition with a model membrane (FIG. 7) the last predicted residue to lie within the bilayer is H722, in agreement with glycosylation mapping studies (Stefansson et al., 2004). To test this model, we mutated two basic residues in the S1-S2 loop: mutation of K322 (K322D), which points towards the bilayer in our model, prevented talin activation, while mutation of K320 (K320D), which points away from the bilayer, had no effect (FIG. 6B). We speculate therefore that F3-membrane interactions, together with the formation of a β-tail helix in intimate contact with F3, make significant contributions to the energy required to stabilize the integrin activated state. In the context of a complete FERM domain, this orientation and location of F3, in which the MP helix points vertically through the membrane, also brings the surfaces of the F1 and F2 domains into close apposition with the membrane. We note that in the F2 domain, four lysines (263, 268, 272 and 274) also appear appropriately positioned to interact with the membrane. This orientation of the FERM domain on the membrane surface is similar to that proposed previously for a radixin-ICAM-2 complex (Hamada et al. 2003).

Figure 13:
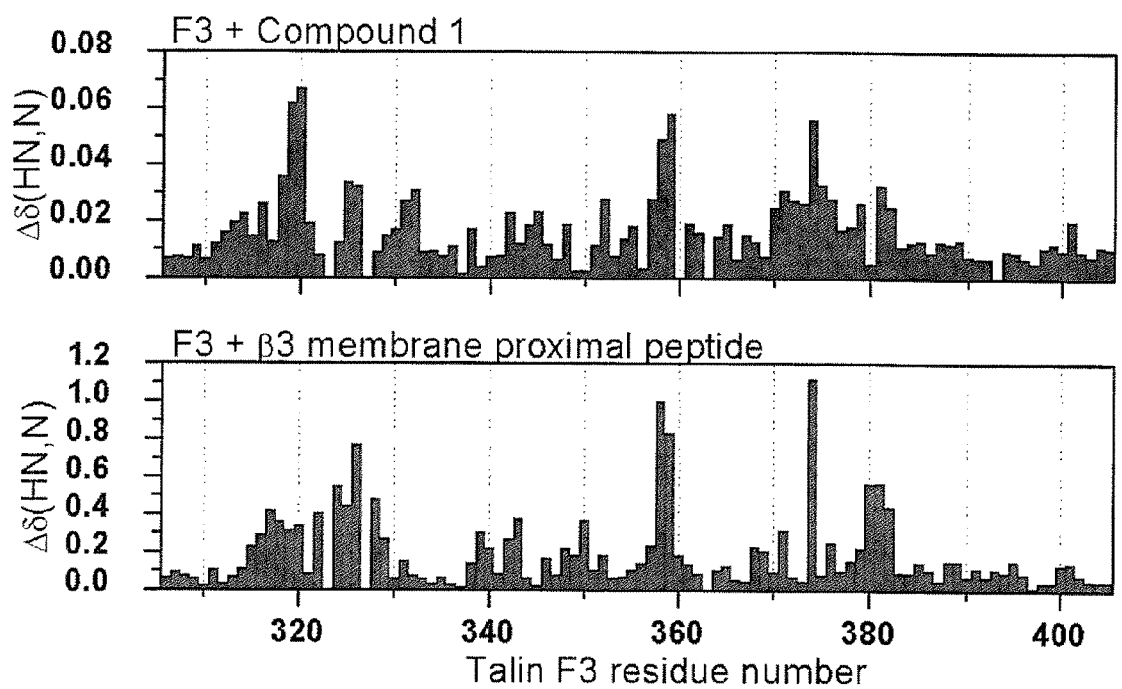
FIG. 13 shows evidence of one compound (selected from a large screening of compounds) binding in the membrane proximal interaction site of the beta3 integrin tail. A. Graph of the pattern of residues affected by binding to the membrane proximal region of the beta3 integrin tail and that of Compound 1. B. The structure of Compound 1.
Figure 13:
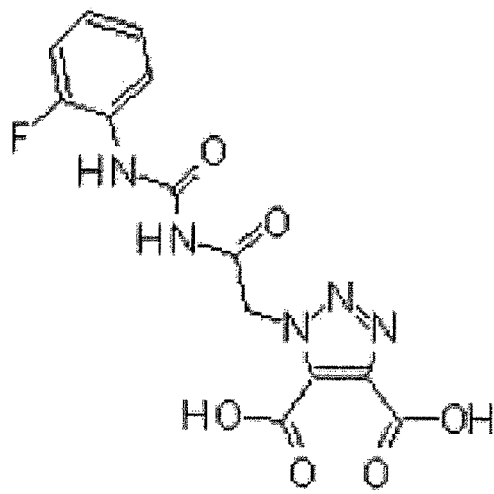

Approximately 60,000 compounds were screened in silica using the software FlexX. One hundred and thirty five of these compounds were selected based on the calculation results and manual clustering. These compounds were screened in vitro for interaction with the talin PTB domain using NMR spectroscopy. Results indicated around 15 of the compounds bound in some way to talin, with one of the compounds showing indications of binding in the membrane proximal interaction site (see FIG. 13). As FIG. 13 indicates, the pattern of residues affected by binding to the membrane proximal region of the β3 integrin tail, is similar to that affected by the compound tested, indicating they may share their site of interaction.

In summary, we have demonstrated the structural basis for the unique ability of talin to activate integrins. The specific interface identified here completes the molecular picture of the talin/β3 interaction and provides a target for the design of therapeutics aimed at disrupting integrin activation while leaving talin's other activities intact. Finally, we provide a structural template for mutational studies to define the biological role of talin's ability to activate integrins in cells and ultimately in whole animals.

Additional data is shown in FIGS. 8-12, showing the structural basis of integrin activation by talin, as well as in Tables 1-3.

TABLE 1

Experimental Restraints and Structural Studies for the Structure of the Talin F3 Domain in Complex with the Chimeric β3-Integrin/PIPKIγ Peptide

Experimental restraints

|  | Talin F3 | Chimeric peptide |
|---|---|---|
| NOE (non-redundant) | 319 | 147 |
| Intraresidue (i, j = 0) | 455 | 143 |
| Sequential (i-j = 1) | 236 | 78 |
| Short range (i-j < 5) | 469 | 7 |
| Long range (i-j ≧ 5) | 24 | 5 |
| Ambiguous | 319 | 147 |
| Intermolecular |  | 138[a] |
| Hydrogen bonds[b] | 29 | 5 |
| Dihedral angles |  |  |
| TALOS$_\phi$ | 58 |  |
| TALOS$_\psi$ | 57 |  |
| $^3J_{HNHA}\phi$ | 11 |  |
| Total number of restraints | 2175 |  |

Structure quality

|  | 20 Structure ensemble | Minimized average structure |
|---|---|---|
| *RMSDs from experimental restraints* |  |  |
| Distance restraints (Å) | 0.0083 ± 0.0008 | 0.0094 |
| Dihedral angles (°) | 0.55 ± 0.05 | 0.69 |
| Distance violations > 0.3 Å | 0 | 0 |
| Dihedral angle violations > 5° | 0 | 0 |
| *RMSDs from idealized geometry* |  |  |
| Bonds (Å) | 0.012 ± 0.004 | 0.003 |
| Angles (°) | 0.59 ± 0.01 | 0.36 |
| Impropers (°) | 0.28 ± 0.1 | 0.21 |

|  | F3 | Peptide | Complex | F3 | Peptide | Complex |
|---|---|---|---|---|---|---|
| Ramachandran statistics[c] |  |  |  |  |  |  |
| Most favoured regions | 92.4% | 99.5% | 94.1% | 94.4% | 100.0% | 95.7% |
| Additionally allowed regions | 7.6% | 0.2% | 5.9% | 5.6% | 0.0% | 4.3% |
| Generally allowed regions | 0.0% | 0.0% | 0.0% | 0.0% | 0.0% | 0.0% |
| Disallowed regions | 0.0% | 0.2% | 0.1% | 0.0% | 0.0% | 0.0% |
| Structure precision[c,d] |  |  |  |  |  |  |
| Backbone atoms (Å) | 0.261 | 0.262 | 0.296 |  |  |  |
| All heavy atoms (Å) | 0.645 | 0.898 | 0.735 |  |  |  |

[a]Twenty-seven intermolecular NOEs were found in the [$^3$H—$^{15}$N]-NOESY-HSQC spectrum on U-$^{15}$N F3 and unlabelled chimeric peptide (1:1.2, 90% $H_2O/D_2O$), 99 from the 2DNOESY spectrum of unlabelled F3 and chimeric peptide (1:1, 99.96% $D_2O$) and 42 from the 2DNOESY spectrum of U-$^{15}$N, 3H F3 and unlabelled chimeric peptide (1:3:1, 90% $H_2O/D_2O$).
[b]Hydrogen bond restraints were applied between amide oxygen and nitrogen atoms and between amide proton and oxygen atoms.
[c]Mobile residues ($^{15}$N=$^1$H NOE < 0.65) of the F3 domain were excluded. Included are residues 313-319, 325-328, 330-371, 378-401. Only well-ordered peptide residues were included. Included residues are 723-735 and 737-739 from the β3 integrin and residues 643-649 from the PIPKIγ peptide (numbered 740-746 in the deposited pdb structures).
[d]RMSD from the average structure

TABLE 2

Summary of Isothermal Calorimetry Data

| Protein | Peptide | Kd (nM) |
|---|---|---|
| Talin F3 wt | β3 chimera | 140 ± 11 |
| Talin F3 wt | β3 chimera F727A | 118 ± 26 |
| Talin F3 wt | β3 chimera F730A | 105 ± 50 |
| Talin F3 L325R | β3 chimera | 212 ± 29 |
| Talin F3 W359A | β3 chimera | 106000 ± 49000 |
| Talin F3 Q381V | β3 chimera | 135 ± 35 |

Reported values are the average of at least two independent measurements.

TABLE 3

Average Number of Steric Clashes Between the αIIb Tail and the Talin F3 Domain for Calculated αIIb and β3 Integrin Complexes

| | 0.5-1.0 Å | 1.0-2.0 Å | >2.0 Å |
|---|---|---|---|
| 1M8O[b] | 0.4 | 0.1 | 0.0 |
| 1KUP[c] | 0.4 | 0.0 | 0.0 |
| 1KUZ[d] | 186.7 | 189.8 | 32.5 |
| Gottschalk model | 150.6 | 160.2 | 31.8 |

[a]There are a three rather different NMR structures in the PDB database. Two (PDB accession codes 1KUP and 1KUZ) come from a single study of relatively short peptides derived from the α and β cytoplasmic tails (Weljie et al., 2002); the other (1M80) comes from a study of an α-tail in a 10:1 concentration ratio with a β-tail attached to meliose binding protein (Vinogradova et al., 2002).
We were also kindly provided with the coordinates of a model of the membrane spanning regions, plus parts of the cytoplasmic tails, by Prof. K. Gottschalk (Gottschalk, 2005). To assess the extent to which our newly determined structure of the β-tail/talin F3 complex interfered with these structures we measured the number of steric clashes that occurred when β-tail residues 723-726 from each structure were overlaid.
The top 10 structures of each α/β complex were overlaid on each of the top 10 talin/chimera complex structures. The number of steric clashes for each superimposition was calculated using MOLMOL and the average obtained for each α/β complex is presented. The single Gottschalk model was overlaid with the top 10 talin/chimera calculated structures.
[b]Residues 28-32 from 1M8O were overlaid with residues 723-727 of the talin/chimera complex. Note that 98% (47 out of 48) of the violations found for this superimposition involved the putative salt-bridge forming R995 from the alpha chain.
[c]Residues 19-23 from 1KUP were overlaid with residues 723-727, of the talin/chimera complex. 61% (25 out of 41) of the violations found for this superimposition involved R995 from the alpha chain.
[d]Residues 20-24 from 1KUZ were overlaid with residues 724-728, of the talin/chimera complex.

Experimental Procedures
Peptides

Peptides were synthesized commercially by Alta Bioscience (Birmingham, UK) or EZBiolab (Westfield, USA), or produced as a GST-β3 recombinant fusion protein with the peptide liberated by thrombin digestion. All peptides were further purified using reverse phase high performance liquid chromatography and validated by electrospray ionization mass spectrometry.

Labeled Protein Preparation

U-$^{15}$N labeled talin F3 domain was expressed and purified as described previously (de Pereda et al., 2005). U-$^{15}$N labeled DOK1 PTB domain (residues 154-256; Swiss-Prot Q99704) was sub-cloned into the pGEX-6P2 vector and produced using the same methods. U-$^{15}$N,$^{13}$C and U-$^{15}$N,$^{2}$H doubly-labeled talin was produced in the same way, using $^{13}$C-glucose or D6-glucose and D$_2$O.

NMR Spectroscopy

All NMR experiments were carried out at 25° C. on spectrometers equipped with Oxford Instruments super-conducting magnets (500, 600 and 750 MHz $^1$H operating frequencies) and GE/Omega computers.

$^1$H-$^{15}$N-HSQC titrations were performed as previously described (de Pereda et al., 2005). Weighted shifts (Δδ(HN, N)) were calculated using the equation: $\Delta\delta(HN,N) = ((\Delta\delta_{HN}W_{HN})^2 + (\Delta\delta_N W_N)^2)^{1/2}$, where $W_{HN}$ and $W_N$ are weighting factors for the HN and N shifts respectively ($W_{HN}=1$, $W_N=0.154$) (Ayed et al., 2001) and $\Delta\delta = \delta_{bound} - \delta_{free}$. Talin F3 domains in complex with slow-exchanging peptides, as well as mutant F3 domains, were assigned by correlation to the wild-type talin F3 assignments (de Pereda et al., 2005) and confirmed using 3D gradient-enhanced [$^1$H-$^{15}$N]-NOESY-HSQC ($\tau_m$=100 ms) spectra alone, or in combination with [$^1$H-$^{15}$N]-TOCSY-HSQC ($\tau_m$=70 ms) spectra. $^{13}$CO, $^{13}$Cα and $^{13}$Cβ shifts were obtained using a series of 2D $^1$H-$^{15}$N-$^{13}$C experiments (Bersch et al., 2003). Bound peptide shifts were obtained using U—$^{15}$N,$^2$H F3 and unlabeled chimeric peptide (1.3:1). Both bound and unbound chimeric peptide shifts were assigned using 2D NOESY, TOCSY and COSY spectra. DOK PTB domain assignments were obtained previously (unpublished).

NOE data for structure calculations were obtained from a [$^1$H-$^{15}$N]-NOESY-HSQC spectrum on U-$^{15}$N F3 and unlabeled chimeric peptide (1:1.2), a 2D NOESY spectrum on unlabeled F3 and chimeric peptide (1:1) in 99.96% D$_2$O and 2D NOESY spectra from a sample of U-$^{15}$N,$^2$H F3 and unlabeled chimeric peptide (1.3:1) in both 90% H$_2$O/D$_2$O and 99.96% D$_2$O ($\tau_m$=100 ms in each case). Intermolecular NOEs were identified in each NOESY spectra, apart from that of U-$^{15}$N,$^2$H F3 and unlabeled chimeric peptide in 99.96% D$_2$O. All samples contained 50 mM phosphate buffer (pH 6.1) and 100 mM NaCl.

$^3J_{HNCA}$ coupling constants were determined from peak-fitting analysis of $^{15}$N-HMQCJ spectra (Redfield et al., 1991). Heteronuclear $^{15}$N-$^1$H-NOEs were determined from a pair of HSQC experiments recorded with and without $^1$H saturation during the recycle delay (Farrow et al., 1994). NMR experiments were processed using NMRPipe (Delaglio et al., 1995) and visualized with Sparky (www.cgl.ucsf.edu/home/sparky).

Structure Calculation

NOE distance restraints were calibrated on the basis of NOEs from regular secondary structure elements and were grouped into four classes: 1.8-3.0 Å, 1.8-3.8 Å, 1.8-4.6 Å and 1.8-6.0 Å, corresponding to strong, medium, weak and very weak NOEs. Dihedral restraints (Φ/Ψ) were obtained from the TALOS database (Cornilescu et al., 1999). Additional Φ angle restraints were derived from the $^3J_{HNHA}$ coupling constants and a modified Karplus equation (Pardi et al., 1984). Hydrogen bond restraints were incorporated based on hydrogen-exchange data and secondary structure elements identified from initial rounds of structure calculation.

Structure calculations were performed using a simulated annealing protocol within the program CNS v1.1 (Brunger et al., 1998). The initial conformation for the talin F3 domain was derived from the crystal structure of talin in complex with the PIPKIγ peptide (de Pereda et al., 2005), while the chimera peptide started from randomized coordinates. 100 structures were calculated and the top 20 of these were further refined. Floating assignment of prochiral groups was achieved using the SOPHIE procedure (Pickford et al., 2001). During final minimization each group was eased into the pro-R or pro-S position by enforcing the correct bond angles at the prochiral centre. The stereochemical quality of the structures was assessed using the program PROCHECK-NMR (Laskowski et al., 1996). Molecular models were generated using the program MOLMOL (Koradi et al., 1996).

Accession

Chemical shift assignments for the complex have been deposited in the BioMagResBank with the accession number 7150. The coordinates of the calculated structure ensemble and the minimized average structure have been deposited in the Brookhaven Protein Data Bank with the ID codes 2H7D and 2117E, respectively.

Cell Culture, Cell Lines, and Reagents

Chinese hamster ovary (CHO) cells were obtained from American Type Culture Collection (ATCC) and cultured in Dulbecco's modified Eagle's medium with 10% fetal bovine serum (FBS), 1% non-essential amino acids (Sigma), penicillin (50 units/mL) and streptomycin sulfate (50 μg/mL) in a 37° C. tissue culture incubator. The anti-αIIbβ3 antibodies D57, PAC1, and Anti-LIBS6, as well as Ro43-5054, an αIIbβ3-specific peptide-mimetic competitive inhibitor, have been described (Tadokoro et. al. 2003). The D57 antibody was biotinylated with biotin-N-hydroxy-succinimide (Sigma) (B-D57) according to the manufacturer's instructions.

Site Directed Mutagenesis

Site-directed mutations in both the αIIbβ3 subunits and the talin F3 construct were generated using the QuikChange mutagenesis kit (Stratagene). Mutants were confirmed by DNA sequencing.

Flow Cytometry

For experiments to assess the functional effect of point mutants in the β3 tail, CHO cells were co-transfected with pCDM8 plasmids coding for wildtype or mutant sequences of βIIb and β3. Transfection was done using the plus reagent and lipofectamine (Life Technologies); 24 hours later cells were stained with B-D57 and PAC1 in the presence and absence of Ro43-5054 or Anti-LIBS6. The biotinylated monoclonal antibody, B-D57 was used to detect expression of αIIbβ3, while PAC1, an activation specific, monoclonal IgM antibody was used to assess the activation state of the αIIbβ3 integrin. This antibody is an authentic ligand for integrin αIIbβ3 (Abrams et al., 1994) and its binding correlates with the binding of natural ligands, such as fibrinogen (Shattil et al., 1985). Cells were analyzed on a FACScan using both B-D57 and PAC1 antibodies as described previously (Partridge et al., 2005). The geometric mean fluorescence intensity (MFI) of PAC1 staining in the presence of Ro43-5054 (2 μM) was used to estimate non-specific PAC1 binding (F0). The fluorescence intensity in the presence of Anti-LIBS6 was used to estimate maximal PAC1 binding (Fmax), since Anti-LIBS6 directly induces αIIbβ3 binding to PAC1 regardless of the status of cellular activation mechanism (Baker et al., 1997). The activation index was calculated using the formula: $100*(F-F0)/(Fmax-F0)$, where F=MFI under the test condition.

For experiments to assess the functional effect of F3 domain mutations, wildtype or mutant versions of pCDNA3.1 plasmids coding for N-terminally HA-tagged proteins consisting of the F2 and F3 domains of mouse talin (residues 206-405; SwissProt P26039) were transiently transfected into cells stably expressing wildtype αIIbβ3, an αIIb (D723A)β3 mutant, or a αIIbα6Aβ3β1A chimeric integrin (αβPy cells) (Baker et al., 1997). In these experiments eGFP vector was co-transfected as a transfection marker at a HA-F23/eGFP ratio of 20:1.

Calorimetry

Isothermal titration calorimetry (ITC) was performed on a VP-ITC calorimeter (Microcal, Northampton, Mass.). Aliquots (8 μL) of wildtype (KKLLITIHDRKEFAKFEEERAR-AKWVpYSPLHYSAR) (SEQ ID NO: 2) or mutant chimeric peptide were injected into the cell containing wildtype or mutant talin F3 domain. Peptide concentrations were typically 150 to 300 μM while protein concentrations ranged from 25 to 50 μM. For the W359A mutant, the protein concentration was 50 μM and the peptide concentration was 1 mM. Prior to ITC titrations, the peptides and proteins were in 200 mM Tris, 300 mM NaCl, pH 7.5. In each experiment 37 injections were made. The experiments were performed at 23° C. All titrations were performed at least twice and with different protein preparations. Experimental data were analyzed using Microcal Origin software.

The following references are specifically applicable to the Example and to the remainder of the specification and are incorporated herein by reference; these references are referenced in the Example and in the remainder of the specification, where appropriate, by their authors and publication dates as indicated.

Abrams, C., Deng, Y. J., Steiner, B., O'Toole, T., and Shattil, S. J. (1994). Determinants of specificity of a baculovirus-expressed antibody Fab fragment that binds selectively to the activated form of integrin alpha IIb beta 3. J Biol Chem 269, 18781-18788.

Ayed, A., Mulder, F. A., Yi, G. S., Lu, Y., Kay, L. E., and Arrowsmith, C. H. (2001). Latent and active p53 are identical in conformation. Nat Struct Biol 8, 756-760.

Baker, E. K., Tozer, E. C., Pfaff, M., Shattil, S. J., Loftus, J. C., and Ginsberg, M. H. (1997). A genetic analysis of integrin function: Glanzmann thrombasthenia in vitro. Proc Natl Acad Sci USA 94, 1973-1978.

Bennett, J. S. (2005). Structure and function of the platelet integrin alphaIIbbeta3. J Clin Invest 115, 3363-3369.

Bersch, B., Rossy, E., Coves, S., and Brutscher, B. (2003). Optimized set of two-dimensional experiments for fast sequential assignment, secondary structure determination, and backbone fold validation of 13C/15N-labelled proteins. J Biomol NMR 27, 57-67.

Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., et aL (1998). Crystallography & NMR system: A new software suite for macromolecular structure determination. Acta Crystallogr D Biol Crystallogr 54, 905-921.

Calderwood, D. A., Fujioka, Y., de Pereda, J. M., Garcia-Alvarez, B., Nakamoto, T., Margolis, B., McGlade, C. J., Liddington, R. C., and Ginsberg, M. H. (2003). Integrin beta cytoplasmic domain interactions with phosphotyrosine-binding domains: a structural prototype for diversity in integrin signaling. Proc Natl Acad Sci USA 100, 2272-2277.

Calderwood, D. A., Yan, B., de Pereda, J. M., Alvarez, B. G., Fujioka, Y., Liddington, R. C., and Ginsberg, M. H. (2002). The phosphotyrosine binding-like domain of talin activates integrins. J Biol Chem 277, 21749-21758.

Campbell, I. D., and Ginsberg, M. H. (2004). The talin-tail interaction places integrin activation on FERM ground. Trends Biochem Sci 29, 429-435.

Chishti, A. H., Kim, A. C., Marfatia, S. M., Lutchman, M., Hanspal, M., Jindal, H., Liu, S. C., Low, P. S., Rouleau, G. A., Mohandas, N., et al. (1998). The FERM domain: a unique module involved in the linkage of cytoplasmic proteins to the membrane. Trends Biochem Sci 23, 281-282.

Cornilescu, G., Delaglio, F., and Bax, A. (1999). Protein backbone angle restraints from searching a database for chemical shift and sequence homology. J Biomol NMR 13, 289-302.

Critchley, D. R. (2005). Genetic, biochemical and structural approaches to talin function. Biochem Soc Trans 33, 1308-1312.

de Pereda, J. M., Wegener, K. L., Santelli, E., Bate, N., Ginsberg, M. H., Critchley, D. R., Campbell, I. D., and Liddington, R. C. (2005). Structural basis for phosphatidylinositol phosphate kinase type Igamma binding to talin at focal adhesions. J Biol Chem 280, 8381-8386.

Delaglio, F., Grzesiek, S., Vuister, G. W., Zhu, G., Pfeifer, J., and Bax, A. (1995). NMRPipe: a multidimensional spectral processing system based on UNIX pipes. J Biomol NMR 6, 277-293.

Edwards, S. D., and Keep, N. H. (2001). The 2.7 A crystal structure of the activated FERM domain of moesin: an analysis of structural changes on activation. Biochemistry 40, 7061-7068.

Farrow, N. A., Muhandiram, R., Singer, A. U., Pascal, S. M., Kay, C. M., Gish, G., Shoelson, S. E., Pawson, T., Forman-Kay, J. D., and Kay, L. E. (1994). Backbone dynamics of a free and phosphopeptide-complexed Src homology 2 domain studied by 15N NMR relaxation. Biochemistry 33, 5984-6003.

Garcia-Alvarez, B., de Pereda, J. M., Calderwood, D. A., Ulmer, T. S., Critchley, D., Campbell, I. D., Ginsberg, M. H., and Liddington, R. C. (2003). Structural determinants of integrin recognition by talin. Mol Cell 11, 49-58.

Ginsberg, M. H., Partridge, A., and Shattil, S. J. (2005). Integrin regulation. Curr Opin Cell Biol 17, 509-516.

Gottschalk, K. E. (2005). A coiled-coil structure of the alphaIIbbeta3 integrin transmembrane and cytoplasmic domains in its resting state. Structure 13, 703-712.

Hamada, K., Shimizu, T., Matsui, T., Tsukita, S., and Hakoshima, T. (2000). Structural basis of the membrane-targeting and unmasking mechanisms of the radixin FERM domain. Embo J 19, 4449-4462.

Han, B. G., Nunomura, W., Takakuwa, Y., Mohandas, N., and Jap, B. K. (2000). Protein 4.1R core domain structure and insights into regulation of cytoskeletal organization. Nat Struct Biol 7, 871-875.

Horwitz, A., Duggan, K., Buck, C., Beckerle, M. C., and Burridge, K. (1986). Interaction of plasma membrane fibronectin receptor with talin—a transmembrane linkage. Nature 320, 531-533.

Huang, C. L., Cheng, J. C., Liao, C. H., Stern, A., Hsieh, J. T., Wang, C. H., Hsu, H. L., and Tseng, C. P. (2004). Disabled-2 is a negative regulator of integrin alpha(IIb)beta (3)-mediated fibrinogen adhesion and cell signaling. J Biol Chem 279, 42279-42289.

Hughes, P. E., Diaz-Gonzalez, F., Leong, L., Wu, C., McDonald, J. A., Shattil, S. J., and Ginsberg, M. H. (1996). Breaking the integrin hinge. A defined structural constraint regulates integrin signaling. J Biol Chem 271, 6571-6574.

Hughes, P. E., O'Toole, T. E., Ylanne, J., Shattil, S. J., and Ginsberg, M. H. (1995). The conserved membrane-proximal region of an integrin cytoplasmic domain specifies ligand binding affinity. J Biol Chem 270, 12411-12417.

Hynes, R. O. (2002). Integrins: bidirectional, allosteric signaling machines. Cell 110, 673-687.

Koradi, R., Billeter, M., and Wuthrich, K. (1996). MOLMOL: a program for display and analysis of macromolecular structures. J Mol Graph 14, 51-55, 29-32.

Laskowski, R. A., Rullmann, S. A., MacArthur, M. W., Kaptein, R., and Thornton, J. M. (1996). AQUA and PROCHECK-NMR: programs for checking the quality of protein structures solved by NMR. J Biomol NMR 8, 477-486.

Li, W., Metcalf, D. G., Gorelik, R., Li, R., Mitra, N., Nanda, V., Law, P. B., Lear, J. D., Degrado, W. F., and Bennett, J. S. (2005). A push-pull mechanism for regulating integrin function. Proc Natl Acad Sci USA 102, 1424-1429.

Luo, B. H., Carman, C. V., Takagi, S., and Springer, T. A. (2005). Disrupting integrin transmembrane domain heterodimerization increases ligand binding affinity, not valency or clustering. Proc Natl Acad Sci USA 102, 3679-3684.

Papagrigoriou, E., Gingras, A. R., Barsukov, I. L., Bate, N., Fillingham, I. J., Patel, B., Frank, R., Ziegler, W. H., Roberts, G. C., Critchley, D. R., and Emsley, J. (2004). Activation of a vinculin-binding site in the talin rod involves rearrangement of a five-helix bundle. Embo J 23, 2942-2951.

Pardi, A., Billeter, M., and Wuthrich, K. (1984). Calibration of the angular dependence of the amide proton-C alpha proton coupling constants, 3JHN alpha, in a globular protein. Use of 3JHN alpha for identification of helical secondary structure. J Mol Biol 180, 741-751.

Partridge, A. W., Liu, S., Kim, S., Bowie, J. U., and Ginsberg, M. H. (2005). Transmembrane domain helix packing stabilizes integrin alphaIIbbeta3 in the low affinity state. J Biol Chem 280, 7294-7300.

Pickford, A. R., Smith, S. P., Staunton, D., Boyd, J., and Campbell, I. D. (2001). The hairpin structure of the (6)F1 (1)F2(2)F2 fragment from human fibronectin enhances gelatin binding. Embo J 20, 1519-1529.

Redfield, C., Smith, L. J., Boyd, J., Lawrence, G. M., Edwards, R. G., Smith, R. A., and Dobson, C. M. (1991). Secondary structure and topology of human interleukin 4 in solution. Biochemistry 30, 11029-11035.

Rees, D. J., Ades, S. E., Singer, S. J., and Hynes, R. O. (1990). Sequence and domain structure of talin. Nature 347, 685-689.

Shattil, S. J., Hoxie, J. A., Cunningham, M., and Brass, L. F. (1985). Changes in the platelet membrane glycoprotein IIb.IIIa complex during platelet activation. J Biol Chem 260, 11107-11114.

Smith, W. S., Nassar, N., Bretscher, A., Cerione, R. A., and Karplus, P. A. (2003). Structure of the active N-terminal domain of Ezrin. Conformational and mobility changes identify keystone interactions. J Biol Chem 278, 4949-4956.

Stefansson, A., Armulik, A., Nilsson, I., von Heijne, G., and Johansson, S. (2004). Determination of N- and C-terminal borders of the transmembrane domain of integrin subunits. J Biol Chem 279, 21200-21205.

Tadokoro, S., Shattil, S. J., Eto, K., Tai, V., Liddington, R. C., de Pereda, J. M., Ginsberg, M. H., and Calderwood, D. A. (2003). Talin binding to integrin beta tails: a final common step in integrin activation. Science 302, 103-106.

Tanentzapf, G., and Brown, N. H. (2006). An interaction between integrin and the talin FERM domain mediates integrin activation but not linkage to the cytoskeleton. Nat Cell Biol.

Uhlik, M. T., Temple, B., Bencharit, S., Kimple, A. S., Siderovski, D. P., and Johnson, G. L. (2005). Structural and evolutionary division of phosphotyrosine binding (PTB) domains. J Mol Biol 345, 1-20.

Ulmer, T. S., Calderwood, D. A., Ginsberg, M. H., and Campbell, I. D. (2003). Domain-specific interactions of talin with the membrane-proximal region of the integrin beta3 subunit. Biochemistry 42, 8307-8312.

Vinogradova, O., Vaynberg, J., Kong, X., Haas, T. A., Plow, E. F., and Qin, J. (2004). Membrane-mediated structural transitions at the cytoplasmic face during integrin activation. Proc Natl Acad Sci USA 101, 4094-4099.

Vinogradova, O., Velyvis, A., Velyviene, A., Hu, B., Haas, T., Plow, E., and Qin, J. (2002). A structural mechanism of integrin alpha(IIb)beta(3) "inside-out" activation as regulated by its cytoplasmic face. Cell 110, 587-597.

Weljie, A. M., Hwang, P. M., and Vogel, H. J. (2002). Solution structures of the cytoplasmic tail complex from platelet integrin alpha IIb- and beta 3-subunits. Proc Natl Acad Sci USA 99, 5878-5883.

The present invention provides a new therapeutic target for treatment of diseases and conditions associated with the activation of integrin $\beta_3$, including heart disease such as myocardial infarction, tumor metastasis, and inflammatory conditions, including autoimmune diseases. The new therapeutic target provides for specific disruption of the molecular interaction between integrin $\beta_3$ and talin, which provides a more specific therapeutic effect without significant side effects that have limited the use of other integrin-based therapeutics in many patients.

The chimeric peptides, muteins, nucleic acid molecules, and screening methods of the present invention possess industrial applicability for treatment of diseases and conditions associated with the activation of integrin $\beta_3$ and for the detection of agents suitable for the treatment of such diseases and conditions.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

The invention claimed is:

1. A chimeric peptide comprising:
   (a) a tryptophan (W) residue that binds to a pocket on the surface of talin molecule;
   (b) a membrane proximal (MP) peptide of $\beta_3$ integrin tail comprising the amino acid sequence KLLITIHDRKEFAKFEEERARAK (SEQ ID NO: 7), wherein at least one F residue is mutated, on the aminoterminal side of the tryptophan residue of (a); and
   (c) a C-terminal peptide PIPKIγ comprising the amino acid sequence VpYSPLHYSAR (SEQ ID NO: 8) on the carboxyl-terminal side of the tryptophan residue of (a) to form a binding site in conjunction with (a) and (b); wherein the chimeric peptide is soluble and has higher affinity for talin than $\beta_3$ integrin tail.

2. The chimeric peptide of claim 1, wherein at least one F residue in SEQ ID NO:7 is mutated with A residue.

3. The chimeric peptide of claim 1, wherein both F residues in SEQ ID NO:7 are mutated with A residues.

4. The chimeric peptide of claim 1, wherein said C-terminal peptide of PIPKIγ is the amino acid sequence VpYSPLHYSAR (SEQ ID NO: 8).

5. The chimeric peptide of claim 1, wherein said chimeric peptide is expressed by a host cell transformed or transfected with a nucleotide encoding said chimeric peptide.

6. The chimeric peptide of claim 1, wherein said chimeric peptide is chemically synthesized.

* * * * *